United States Patent
Sode et al.

(10) Patent No.: US 11,505,596 B2
(45) Date of Patent: Nov. 22, 2022

(54) MUTANT CYTOCHROME PROTEIN LACKING CERTAIN HEME DOMAINS AND USE THEREOF

(71) Applicant: ARKRAY, Inc., Kyoto (JP)

(72) Inventors: Koji Sode, Tokyo (JP); Junko Shimazaki, Tokyo (JP); Kazushige Mori, Tokyo (JP); Katsuhiro Kojima, Tokyo (JP)

(73) Assignee: ARKRAY, INC., Kyoto (JP)

( * ) Notice: Subject to any disclaimer, the term of this patent is extended or adjusted under 35 U.S.C. 154(b) by 0 days.

(21) Appl. No.: 17/158,560

(22) Filed: Jan. 26, 2021

(65) Prior Publication Data

US 2021/0155675 A1    May 27, 2021

Related U.S. Application Data

(62) Division of application No. 16/026,316, filed on Jul. 3, 2018, now Pat. No. 10,927,162.

(30) Foreign Application Priority Data

Jul. 4, 2017  (JP) .............................. JP2017-131345

(51) Int. Cl.
| | | |
|---|---|---|
| *C07K 14/80* | (2006.01) | |
| *C12N 9/02* | (2006.01) | |
| *C12Q 1/00* | (2006.01) | |
| *C12N 9/04* | (2006.01) | |

(52) U.S. Cl.
CPC ............ *C07K 14/80* (2013.01); *C12N 9/0004* (2013.01); *C12N 9/0006* (2013.01); *C12Q 1/004* (2013.01); *C12Q 1/006* (2013.01); *C12Y 101/9901* (2013.01)

(58) Field of Classification Search
None
See application file for complete search history.

(56) References Cited

U.S. PATENT DOCUMENTS

| 7,713,718 | B1 | 5/2010 | Sode et al. |
|---|---|---|---|
| 8,354,112 | B2 | 1/2013 | Sode |
| 9,353,395 | B2 | 5/2016 | Sode |
| 10,351,892 | B2* | 7/2019 | Kojima ................... C12Q 1/006 |
| 2004/0023330 | A1* | 2/2004 | Sode ..................... C12N 9/0006 435/189 |
| 2006/0258959 | A1 | 11/2006 | Sode |
| 2009/0177067 | A1 | 7/2009 | Sode |

FOREIGN PATENT DOCUMENTS

| EP | 2447358 A1 | 5/2012 |
|---|---|---|
| WO | 2005/023111 A1 | 3/2005 |

OTHER PUBLICATIONS

Hibino et al., "Construction of a protein-engineered variant of D-fructose dehydrogenase for direct electron transfer-type bioelectrocatalysis," Electrochemistry Communications, 77: 112-115 (2017).
Office Action issued in corresponding European Patent Application No. 18181763.6 dated Aug. 7, 2020.
Extended European Search Report issued in corresponding European Patent Application No. 18181763.6 dated Nov. 6, 2018.
Yamashita et al., "Mutagenesis Study of the Cytochrome c Subunit Responsible for the Direct Electron Transfer-Type Catalytic Activity of FAD-Dependent Glucose Dehydrogenase," International Journal of Molecular Sciences, 19: 931 (2018).
Chica et al., "Semi-rational approaches to engineering enzyme activity: combining the benefits of directed evolution and rational design," Current Opinion in Biotechnology, 16 (4): 378-384 (2005).
Singh et al., "Protein Engineering Approaches in the Post-Genomic Era," Current Protein and Peptide Science, 18: 1-11 (2017).
Accession B9B4W9 (2009).
Bomscheuer et al., "Survey of Protein Engineering Strategies," Current Protocols in Protein Science, 26.7.1-26.7.14 (2011).
Yoshikuni et al., "Pathway engineering by designed divergent evolution," Current Opinion in Clinical Biology, 11 (2): 233-239 (2007).

* cited by examiner

*Primary Examiner* — Christian L Fronda
(74) *Attorney, Agent, or Firm* — Morgan, Lewis & Bockius LLP

(57) ABSTRACT

A mutant cytochrome protein originated from a cytochrome protein having three heme-binding domains, which mutant cytochrome protein lacks the first heme-binding domain and the second heme-binding domain as counted from the N-terminus, is provided. The mutant cytochrome protein may lack a region(s) containing the first and second heme-binding domains.

18 Claims, 1 Drawing Sheet

Specification includes a Sequence Listing.

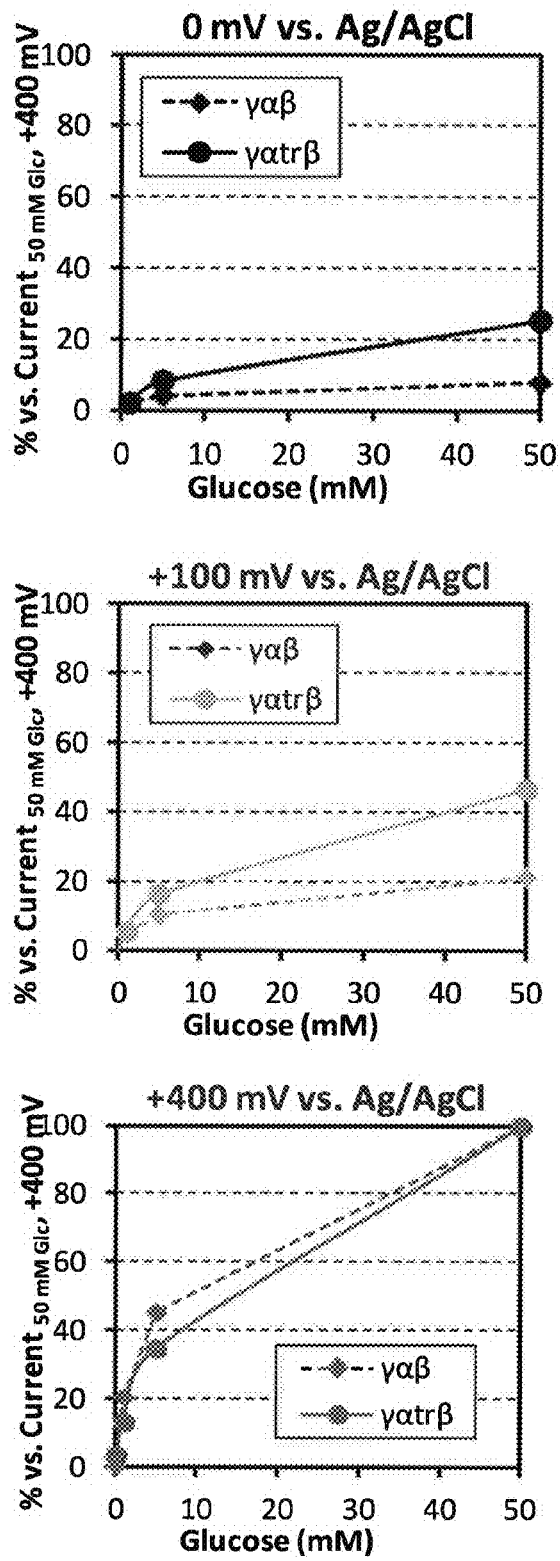

MUTANT CYTOCHROME PROTEIN LACKING CERTAIN HEME DOMAINS AND USE THEREOF

SEQUENCE LISTING SUBMISSION VIA EFS-WEB

A computer readable text file, entitled "SequenceListing.txt," created on or about Jul. 2, 2018 with a file size of about 56 kb contains the sequence listing for this application and is hereby incorporated by reference in its entirety.

TECHNICAL FIELD

The present invention relates to a mutant cytochrome protein capable of electron transfer even at a low electric potential. The mutant cytochrome protein according to one embodiment of the present invention can be suitably used for biosensors and the like, and is useful in the fields of biochemistry, medicine, and the like.

BACKGROUND ART

Cytochrome protein is known as an electron acceptor protein, and used as an electrochemical sensor by formation of a complex with a catalytic subunit of an oxidoreductase.

For example, WO 2005/023111 discloses use of a complex of the catalytic subunit (α-subunit) and the cytochrome c subunit (β-subunit) of glucose dehydrogenase derived from a Burkholderia microorganism as a biosensor. Such a biosensor is used for measurement of the glucose concentration or the like in a biological sample. For more accurate measurement, the measurement sensitivity needs to be increased by, for example, modification of the protein.

The mutants of electrochemical sensor proteins that have been studied so far are mainly mutants of a catalytic subunit, and mutants of a cytochrome protein have been hardly studied.

SUMMARY OF THE INVENTION

In measurement of a target substance using a biosensor that monitors the oxidation-reduction current, it is preferred to reduce the oxidation-reduction potential to within the range in which electron transfer between an enzyme or an enzyme complex and an electrode can be monitored, from the viewpoint of reduction of influences of reducing substances contained in the sample.

However, in cases where the oxidation-reduction current is monitored using a conventional naturally occurring cytochrome protein as an electron acceptor protein, application of a high electric potential to the electrode is required. For example, in Example 7 of WO 2005/023111, an electric potential of +350 nM is applied with respect to a silver-silver chloride electrode. At this electric potential, there is a concern that the measured value may be positively biased due to oxidation of reducing substances such as ascorbic acid and acetaminophen.

In view of such a problem, one aspect of the present invention is to provide a mutant electron acceptor subunit protein that can be used for a biosensor capable of measuring a target substance by application of a low electric potential.

The present inventors prepared a mutant cytochrome c protein lacking a region containing the first heme-binding domain and the second heme-binding domain as counted from the amino-terminus. The present inventors then carried out evaluation of a biosensor using this protein. Surprisingly, as a result, the present inventors found that a mutant cytochrome c protein lacking a region(s) containing the first and second heme-binding domains is capable of accepting an electron from a catalytic subunit irrespective of the fact that the protein has only one heme-binding domain (third heme-binding domain), allowing an electric current to flow depending on the target substance even at an electric potential lower than those in conventional cases, thereby completed the present invention.

One aspect of the present invention is to provide a mutant cytochrome protein originated from a cytochrome protein having three heme-binding domains, the mutant cytochrome protein lacking the first heme-binding domain and the second heme-binding domain as counted from the N-terminus.

Another aspect of the present invention is to provide the mutant cytochrome protein as described above, wherein said mutant cytochrome protein lacks a region(s) comprising the first and second heme-binding domains.

Another aspect of the present invention is to provide the mutant cytochrome protein as described above, wherein the region comprising the first and second heme-binding domains corresponds to the region of amino acids from 43 to 195 of SEQ ID NO:4.

Another aspect of the present invention is to provide the mutant cytochrome protein as described above, wherein the cytochrome protein is a cytochrome c protein.

Another aspect of the present invention is to provide the mutant cytochrome protein as described above, wherein the cytochrome c protein having three heme-binding domains is that of a Burkholderia microorganism.

Another aspect of the present invention is to provide the mutant cytochrome protein as described above, wherein the cytochrome c protein having three heme-binding domains is that of Burkholderia cepacia.

Another aspect of the present invention is to provide the mutant cytochrome protein as described above, wherein the original cytochrome protein having three heme-binding domains comprises an amino acid sequence which is at least 60% identical to SEQ ID NO:4.

Another aspect of the present invention is to provide the mutant cytochrome protein as described above, wherein said mutant cytochrome protein consists of the amino acid sequence selected from the group consisting of:
a) the amino acid sequence of amino acids 314 to 425 of SEQ ID NO:4,
b) the amino acid sequence of amino acids 330 to 425 of SEQ ID NO:4,
c) an amino acid sequence which is the same as the amino acid sequence of amino acids 314 to 425 of SEQ ID NO:4 except that one or several amino acids are substituted, deleted, inserted, and/or added with the proviso that the CXXCH motif of amino acids 334 to 338 is maintained, and
d) an amino acid sequence which is the same as the amino acid sequence of amino acids 330 to 425 of SEQ ID NO:4 except that one or several amino acids are substituted, deleted, inserted, and/or added with the proviso that the CXXCH motif of amino acids 334 to 338 is maintained.

Another aspect of the present invention is to provide the mutant cytochrome protein as described above, wherein said mutant cytochrome protein consists of the amino acid sequence selected from the group consisting of:
a) the amino acid sequence of amino acids 314 to 425 of SEQ ID NO:4,
b) the amino acid sequence of amino acids 330 to 425 of SEQ ID NO:4,
c) an amino acid sequence which is at least 90% identical to the amino acid sequence of amino acids 314 to 425 of SEQ ID NO:4 with the proviso that the CXXCH motif of amino acids 334 to 338 is maintained, and d) an amino acid sequence which is at least 90% identical to the amino acid sequence of amino acids 330 to 425 of SEQ ID NO:4 with the proviso that the CXXCH motif of amino acids 334 to 338 is maintained.

Another aspect of the present invention is to provide a DNA encoding the mutant cytochrome protein as described above.

Another aspect of the present invention is to provide a recombinant vector comprising the DNA as described above.

Another aspect of the present invention is to provide a cell transformed with the recombinant vector as described above.

Another aspect of the present invention is to provide an oxidoreductase-cytochrome complex comprising the mutant cytochrome protein as described above and a catalytic subunit protein of an oxidoreductase.

Another aspect of the present invention is to provide the oxidoreductase-cytochrome complex as described above, wherein the oxidoreductase is glucose dehydrogenase.

Another aspect of the present invention is to provide a biosensor comprising an enzyme electrode comprising the oxidoreductase-cytochrome complex as described above.

Another aspect of the present invention is to provide a method for measuring a measurement target substance, comprising adding a sample to the biosensor as described above, applying an electric potential, measuring the response current, and then calculating the concentration of the measurement target substance contained in the sample based on the response current. In particular, the method serves to measure the concentration of the target substance in a sample.

Another aspect of the present invention is to provide the method as described above, wherein an electric potential of 0 to +300 mV is applied to the enzyme electrode with respect to a silver-silver chloride electrode.

The present invention enables construction of an electrochemical biosensor that operates at an electric potential lower than those in conventional cases (for example, by application of 0 to +300 mV, 0 to +150 mV, or 0 to +100 mV with respect to a silver-silver chloride electrode), thereby allowing accurate measurement of a target substance such as glucose by suppression of interference by reducing substances in the sample.

BRIEF DESCRIPTION OF THE DRAWINGS

FIG. 1 is a diagram illustrating the results of chronoamperometry using a glucose sensor containing a glucose dehydrogenase (GDH) complex having a wild-type β-subunit or a glucose sensor containing a GDH complex having an N-terminal region-deleted β-subunit (the electric potential applied was 0, +100, or +400 mV).

EMBODIMENTS FOR CARRYING OUT THE INVENTION

Embodiments of the present invention are described below in detail.

The mutant cytochrome protein according to one embodiment of the present invention is a mutant of a cytochrome protein having three heme-binding domains, which mutant lacks the first heme-binding domain and the second heme-binding domain as counted from the N-terminus. The protein originates from a cytochrome protein having three heme-binding domains. As used herein, a protein which "originates" refers to a protein which is derived from the parent/original cytochrome protein to provide the mutated cytochrome protein, e.g. by mutation. The original cytochrome protein contains the three heme-binding domains.

Cytochrome protein has three heme-binding domains, and the first, second, and third heme-binding domains as counted from the N-terminus are referred to as first, second, and third heme-binding domains, respectively, in the present specification. A heme-binding domain is generally represented as CXXCH (SEQ ID NO:5) (wherein X represents an arbitrary amino acid), and the mutant cytochrome protein according to one embodiment of the present invention is obtained by modifying a wild type cytochrome protein such that it lacks the first and second heme-binding domains.

Here, "modified such that it lacks the first and second heme-binding domains" means that the protein lacks the first and second CXXCH motifs.

The lack of the CXXCH motifs includes lack of a region(s) containing the CXXCH motifs. The protein may lack a region containing the first heme-binding domain and a region containing the second heme-binding domain separately, or may lack a region containing the first and second heme-binding domains.

The cytochrome protein may be a cytochrome c protein. Examples of the cytochrome c protein include the cytochrome c protein of *Burkholderia cepacia* represented by SEQ ID NO:4 (β-subunit of glucose dehydrogenase).

The cytochrome c protein of *Burkholderia cepacia* is described below as a representative example.

In SEQ ID NO:4, the first heme-binding domain (amino acids 43 to 47), the second heme-binding domain (amino acids 191 to 195), and the third heme-binding domain (amino acids 334 to 338) are present. The lack of the first heme-binding domain and the second heme-binding domain may be achieved by lacking (e.g. by deletion of) a region containing the first and second heme-binding domains (amino acids 43 to 195).

As long as the third heme-binding domain is maintained and allows the protein to function as a mutant cytochrome c protein, that is, as long as the electron transfer ability is maintained, the lack of the region containing the first and second heme-binding domains (amino acids 43 to 195) may be lack of at least this region, and may be lack of not only this region, but also amino acids before and after this region in SEQ ID NO:4. For example, the protein may lack the region from the N-terminus to the amino acid at position 195 of SEQ ID NO:4. An example of the mutant cytochrome c protein lacking a region containing the first and second heme-binding domains is the mutant cytochrome c protein composed of amino acid positions 314 to 425 or 330 to 425 of SEQ ID NO:4. However, in these sequences, an arbitrary tag sequence(s) and/or signal sequence(s) (for example, amino acids 1 to 27 of SEQ ID NO:4) may be added to the N-terminal side and/or the C-terminal side.

The mutant cytochrome protein according to one embodiment of the present invention is not limited to the amino acid sequence consisting of amino acids 314 to 425 of SEQ ID NO:4 or the amino acid sequence consisting of amino acids 330 to 425 of SEQ ID NO:4 itself, and may be a sequence which is the same as this sequence except that one or several amino acids in a region(s) other than the third heme-binding domain (amino acids 334 to 338) are substituted, deleted, added, and/or inserted, as long as the electron transfer ability is maintained. The term "one or several" herein means, for example, 1 to 20, 1 to 10, 1 to 8, 1 to 5, or 1 to 3, i.e. 1, 2 or 3. The substitution may be conservative substitution. "Conservative substitution" means substitution between amino acids having similar properties, such as substitution between acidic amino acids, substitution between neutral amino acids, or substitution between basic amino acids. To the N-terminal side of the amino acid sequence consisting of amino acids 314 to 425 of SEQ ID NO:4, part of the C-terminal sequence of the amino acid sequence consisting of amino acids 196 to 313 of SEQ ID NO:4 may be added. To the N-terminal side of the amino acid sequence consisting of amino acids 330 to 425 of SEQ ID NO:4, part of the C-terminal sequence of the amino acid sequence consisting of amino acids 196 to 329 of SEQ ID NO:4 may be added As long as the third heme-binding domain (amino acids 334 to 338) is maintained and the electron transfer ability is maintained, the mutant cytochrome c protein may be a protein consisting of an amino acid sequence with a sequence identity of not less than 80%, not less than 90%, or not less than 95% to the amino acid sequence consisting of amino acids 314 to 425 of SEQ ID NO:4 or the amino acid sequence consisting of amino acids 330 to 425 of SEQ ID NO:4.

SEQ ID NO:4 is the amino acid sequence of the GDH β-subunit of the *Burkholderia cepacia* KS1 strain. The KS1 strain has been deposited with International Patent Organism Depositary, National Institute of Advanced Industrial Science and Technology (at present, National Institute of Technology and Evaluation (NITE), 2-5-8 Kazusakamatari, Kisarazu-shi, Chiba 292-0818, Japan) under accession No. FERM BP-7306 as of Sep. 25, 2000.

The cytochrome c protein before the introduction of the modification (original cytochrome c protein) is not limited to the cytochrome c protein of *Burkholderia cepacia* represented by SEQ ID NO:4 as long as it has the first, second, and third heme-binding domains. For example, a homologue of SEQ ID NO:4 may be used, and the homologue may have an identity of not less than 60%, not less than 80%, or not less than 90% or 95% to SEQ ID NO:4.

The amino acid sequence of the cytochrome c protein having a sequence identity of not less than 60% to SEQ ID NO:4 may be a cytochrome c protein of the genus *Burkholderia*. Examples of such a cytochrome c protein include the cytochrome protein of the *Burkholderia cepacia* J2315 strain (SEQ ID NO:6), the cytochrome c protein of *Burkholderia cenocepacia* (SEQ ID NO:7), the cytochrome c protein of *Burkholderia multivorans* (SEQ ID NO:8), the cytochrome c protein of *Burkholderia ubonensis* (SEQ ID NO:9), the cytochrome c protein of *Burkholderia stagnalis* (SEQ ID NO:10), and the cytochrome c protein of *Burkholderia thailandensis* (SEQ ID NO:11).

The cytochrome protein may be a cytochrome protein of a genus other than *Burkholderia*, such as a cytochrome protein of *Ralstonia solanacearum* (SEQ ID NO:12) or a cytochrome protein of *Ralstonia pickettii* (SEQ ID NO:13). The cytochrome protein is not limited to these, and may be a cytochrome c protein derived from another organism. Examples of the amino acid sequences of cytochrome c proteins having a sequence identity of not less than 60% to SEQ ID NO:4 are shown below with accession numbers for Protein Database of National Center for Biotechnology Information (NCBI). In each of these sequences, three heme-binding domains are present. The mutant cytochrome protein can be obtained by deleting the first heme-binding domain and the second heme-binding domain as counted from (i.e. starting from) the amino-terminus.

WP_006403391.1 MULTISPECIES: cytochrome C [*Burkholderia*]
AAQ06608.1 glucose dehydrogenase beta subunit [*Burkholderia cepacia*]
WP_006396899.1 cytochrome C [*Burkholderia multivorans*] (SEQ ID NO:8)
SAJ95286.1 gluconate 2-dehydrogenase (acceptor) [*Burkholderia multivorans*]
WP_006412653.1 cytochrome C [*Burkholderia multivorans*]
WP_060041792.1 cytochrome C [*Burkholderia multivorans*]
WP_060112921.1 cytochrome C [*Burkholderia multivorans*]
WP_060182288.1 cytochrome C [*Burkholderia multivorans*]
WP_060151834.1 cytochrome C [*Burkholderia multivorans*]
WP_048804658.1 cytochrome C [*Burkholderia multivorans*]
WP_059786407.1 cytochrome C [*Burkholderia multivorans*]
WP_035955019.1 cytochrome C [*Burkholderia multivorans*]
WP_059585013.1 cytochrome C [*Burkholderia anthina*]
WP_006482958.1 MULTISPECIES: cytochrome C [*Burkholderia cepacia* complex] (SEQ ID NO:6)
WP_048988065.1 cytochrome C [*Burkholderia cenocepacia*] (SEQ ID NO:7)
WP_084751507.1 cytochrome C [*Burkholderia cenocepacia*]
WP_077186512.1 cytochrome C [*Burkholderia cenocepacia*]
WP_069351905.1 cytochrome C [*Burkholderia cenocepacia*]
WP_059783319.1 cytochrome C [*Burkholderia* sp. NRF60-BP8]
WP_060263394.1 cytochrome C [*Burkholderia cenocepacia*]
WP_059836247.1 cytochrome C [*Burkholderia* sp. MSMB1835]
WP_059556637.1 cytochrome C [*Burkholderia seminalis*]
WP_063551853.1 cytochrome C [*Burkholderia territorii*]
WP_060310848.1 cytochrome C [*Burkholderia anthina*]
WP_034187893.1 MULTISPECIES: cytochrome C [*Burkholderia cepacia* complex]
WP_059789576.1 cytochrome C [*Burkholderia* sp. MSMB1072]
WP_059500343.1 MULTISPECIES: cytochrome C [*Burkholderia cepacia* complex]
WP_034204695.1 MULTISPECIES: cytochrome C [*Burkholderia cepacia* complex]
WP_011882359.1 cytochrome C [*Burkholderia vietnamiensis*]
WP_060968838.1 cytochrome C [*Burkholderia anthina*]
WP_077204198.1 cytochrome C [*Burkholderia cenocepacia*]
WP_050012790.1 cytochrome C [*Burkholderia cenocepacia*]
WP_011547563.1 MULTISPECIES: cytochrome C [*Burkholderia*]
WP_014724780.1 MULTISPECIES: cytochrome C [*Burkholderia*]
WP_059453668.1 cytochrome C [*Burkholderia vietnamiensis*]
WP_034195126.1 MULTISPECIES: cytochrome C [*Burkholderia*]

WP_027812584.1 cytochrome C [*Burkholderia cenocepacia*]
WP_059720348.1 cytochrome C [*Burkholderia vietnamiensis*]
WP_059548127.1 cytochrome C [*Burkholderia vietnamiensis*]
WP_044843288.1 cytochrome C [*Burkholderia* sp. USMB20]
WP_059577619.1 cytochrome C [*Burkholderia vietnamiensis*]
WP_059459380.1 cytochrome C [*Burkholderia vietnamiensis*]
WP_059451171.1 cytochrome C [*Burkholderia territorii*]
WP_027780832.1 cytochrome C [*Burkholderia cepacia*]
WP_077217239.1 cytochrome C [*Burkholderia cenocepacia*]
WP_059539736.1 cytochrome C [*Burkholderia diffusa*]
WP_059507572.1 cytochrome C [*Burkholderia territorii*]
AOJ19136.1 cytochrome C [*Burkholderia cenocepacia*]
WP_027806162.1 cytochrome C [*Burkholderia cenocepacia*]
WP_060107812.1 cytochrome C [*Burkholderia territorii*]
WP_059822261.1 cytochrome C [*Burkholderia* sp. MSMB1826]
WP_059464697.1 cytochrome C [*Burkholderia diffusa*]
WP_059240315.1 cytochrome C [*Burkholderia cepacia*]
WP_059734410.1 cytochrome C [*Burkholderia vietnamiensis*]
WP_069227164.1 cytochrome C [*Burkholderia diffusa*]
WP_060118353.1 cytochrome C [*Burkholderia territorii*]
WP_069617959.1 cytochrome C [*Burkholderia* sp. A2]
WP_060347293.1 cytochrome C [*Burkholderia territorii*]
WP_059702517.1 cytochrome C [*Burkholderia vietnamiensis*]
WP_060126789.1 cytochrome C [*Burkholderia territorii*]
WP_069260162.1 cytochrome C [*Burkholderia metallica*]
WP_059978049.1 cytochrome C [*Burkholderia territorii*]
WP_059691288.1 cytochrome C [*Burkholderia* sp. RF4-BP95]
WP_040140035.1 MULTISPECIES: cytochrome C [*Burkholderia cepacia* complex]
WP_011349243.1 cytochrome C [*Burkholderia lata*]
WP_059533875.1 MULTISPECIES: cytochrome C [*Burkholderia cepacia* complex]
WP_059547167.1 cytochrome C [*Burkholderia latens*]
WP_057924955.1 cytochrome C [*Burkholderia ambifaria*]
WP_059607236.1 cytochrome C [*Burkholderia* sp. LA-2-3-30-S1-D2]
WP_039351157.1 MULTISPECIES: cytochrome C [*Burkholderia*]
WP_046548033.1 cytochrome C [*Burkholderia contaminans*]
WP_006752013.1 cytochrome C [*Burkholderia ambifaria*]
WP_014899067.1 cytochrome C [*Burkholderia cepacia*]
WP_006756339.1 cytochrome C [*Burkholderia ambifaria*]
WP_059819259.1 cytochrome C [*Burkholderia* sp. MSMB0856]
WP_011354899.1 cytochrome C [*Burkholderia lata*]
WP_039320755.1 cytochrome C [*Burkholderia* sp. A9]
WP_035974222.1 MULTISPECIES: cytochrome C [*Burkholderia cepacia* complex]
WP_071332428.1 cytochrome C [*Burkholderia contaminans*]
WP_059684703.1 cytochrome C [*Burkholderia* sp. FL-7-2-10-S1-D7]
WP_048252126.1 cytochrome C [*Burkholderia cepacia*]
WP_069251790.1 cytochrome C [*Burkholderia lata*]
WP_011658978.1 cytochrome C [*Burkholderia ambifaria*]
WP_012366204.1 cytochrome C [*Burkholderia ambifaria*]
WP_072438780.1 MULTISPECIES: cytochrome C [*Burkholderia*]
WP_031400525.1 MULTISPECIES: cytochrome C [*Burkholderia*]
WP_034180248.1 cytochrome C [*Burkholderia pyrrocinia*]
WP_043184377.1 cytochrome C [*Burkholderia cepacia*]
WP_059729924.1 cytochrome C [*Burkholderia cepacia*]
WP_059713002.1 cytochrome C [*Burkholderia ubonensis*] (SEQ ID NO:9)
WP_065501791.1 cytochrome C [*Burkholderia stabilis*]
WP_059615074.1 cytochrome C [*Burkholderia ubonensis*]
WP_085037374.1 cytochrome C [*Burkholderia* sp. CAMPA 1040]
WP_060359188.1 cytochrome C [*Burkholderia cepacia*]
WP_060333590.1 cytochrome C [*Burkholderia ubonensis*]
WP_059522548.1 cytochrome C [*Burkholderia cepacia*]
WP_059766841.1 cytochrome C [*Burkholderia ubonensis*]
WP_059637760.1 cytochrome C [*Burkholderia ubonensis*]
WP_040131620.1 MULTISPECIES: cytochrome C [*Burkholderia cepacia* complex]
WP_060052348.1 cytochrome C [*Burkholderia cepacia*]
WP_021162032.1 MULTISPECIES: glucose dehydrogenase [*Burkholderia*]
WP_059666051.1 cytochrome C [*Burkholderia cepacia*]
WP_060375463.1 cytochrome C [*Burkholderia cepacia*]
WP_060371861.1 cytochrome C [*Burkholderia cepacia*]
WP_059697397.1 cytochrome C [*Burkholderia cepacia*]
WP_047903070.1 cytochrome C [*Burkholderia pyrrocinia*]
WP_027791850.1 cytochrome C [*Burkholderia cepacia*]
WP_059552416.1 cytochrome C [*Burkholderia ubonensis*]
WP_060232513.1 cytochrome C [*Burkholderia cepacia*]
WP_059687063.1 cytochrome C [*Burkholderia cepacia*]
WP_060226065.1 cytochrome C [*Burkholderia cepacia*]
WP_060125713.1 cytochrome C [*Burkholderia cepacia*]
WP_059923490.1 cytochrome C [*Burkholderia stagnalis*] (SEQ ID NO:10)
WP_059565670.1 cytochrome C [*Burkholderia stagnalis*]
OJD09200.1 cytochrome C [*Burkholderia* sp. DNA89]
WP_060237338.1 cytochrome C [*Burkholderia pseudomultivorans*]
WP_059707234.1 cytochrome C [*Burkholderia cepacia*]
WP_060362538.1 cytochrome C [*Burkholderia stagnalis*]
WP_060159353.1 cytochrome C [*Burkholderia stagnalis*]
WP_069748432.1 cytochrome C [*Burkholderia stabilis*]
WP_059677336.1 cytochrome C [*Burkholderia cepacia*]
WP_059730424.1 cytochrome C [*Burkholderia ubonensis*]
WP_059813883.1 cytochrome C [*Burkholderia cepacia*]
WP_059993161.1 cytochrome C [*Burkholderia stagnalis*]
WP_060236459.1 cytochrome C [*Burkholderia ubonensis*]
WP_076476708.1 cytochrome C [*Burkholderia ubonensis*]
WP_010089725.1 cytochrome C [*Burkholderia ubonensis*]
WP_060195541.1 cytochrome C [*Burkholderia ubonensis*]
WP_059971786.1 cytochrome C [*Burkholderia pyrrocinia*]
WP_060367052.1 cytochrome C [*Burkholderia ubonensis*]
WP_060016611.1 cytochrome C [*Burkholderia ubonensis*]
WP_059924260.1 cytochrome C [*Burkholderia ubonensis*]
WP_060048488.1 cytochrome C [*Burkholderia ubonensis*]
WP_059892434.1 cytochrome C [*Burkholderia ubonensis*]
WP_059488090.1 cytochrome C [*Burkholderia ubonensis*]
WP_059483872.1 cytochrome C [*Burkholderia ubonensis*]
WP_059865488.1 cytochrome C [*Burkholderia ubonensis*]
WP_059633519.1 cytochrome C [*Burkholderia ubonensis*]
WP_060287380.1 cytochrome C [*Burkholderia ubonensis*]
WP_059853060.1 cytochrome C [*Burkholderia ubonensis*]
WP_059968663.1 cytochrome C [*Burkholderia ubonensis*]

WP_059752176.1 cytochrome C [*Burkholderia ubonensis*]
WP_059532869.1 cytochrome C [*Burkholderia ubonensis*]
WP_059660535.1 cytochrome C [*Burkholderia ubonensis*]
WP_059590294.1 cytochrome C [*Burkholderia ubonensis*]
WP_026043943.1 cytochrome C [*Burkholderia pyrrocinia*]
WP_060264220.1 cytochrome C [*Burkholderia ubonensis*]
WP_060019510.1 cytochrome C [*Burkholderia ubonensis*]
WP_059946330.1 cytochrome C [*Burkholderia ubonensis*]
WP_042588017.1 MULTISPECIES: cytochrome C [*Burkholderia*]
WP_084908871.1 cytochrome C [[*Pseudomonas*] mesoacidophila]
WP_071751088.1 cytochrome C [*Burkholderia ubonensis*]
WP_060094261.1 cytochrome C [*Burkholderia ubonensis*]
WP_059885808.1 cytochrome C [*Burkholderia ubonensis*]
WP_059878406.1 cytochrome C [*Burkholderia ubonensis*]
WP_071852856.1 cytochrome C [*Burkholderia ubonensis*]
WP_060161154.1 cytochrome C [*Burkholderia ubonensis*]
WP_059796027.1 cytochrome C [*Burkholderia ubonensis*]
WP_059835010.1 cytochrome C [*Burkholderia ubonensis*]
WP_059911385.1 cytochrome C [*Burkholderia ubonensis*]
WP_059744627.1 cytochrome C [*Burkholderia ubonensis*]
WP_045565069.1 cytochrome C [*Burkholderia ubonensis*]
WP_060276465.1 cytochrome C [*Burkholderia ubonensis*]
WP_060052180.1 cytochrome C [*Burkholderia ubonensis*]
WP_059877204.1 cytochrome C [*Burkholderia ubonensis*]
WP_059918860.1 cytochrome C [*Burkholderia ubonensis*]
WP_059674217.1 cytochrome C [*Burkholderia ubonensis*]
WP_059626644.1 cytochrome C [*Burkholderia ubonensis*]
WP_059706954.1 cytochrome C [*Burkholderia ubonensis*]
WP_059610359.1 cytochrome C [*Burkholderia ubonensis*]
WP_071751781.1 cytochrome C [*Burkholderia ubonensis*]
WP_060345076.1 cytochrome C [*Burkholderia ubonensis*]
WP_060056668.1 cytochrome C [*Burkholderia ubonensis*]
WP_059867004.1 cytochrome C [*Burkholderia ubonensis*]
WP_059846198.1 cytochrome C [*Burkholderia ubonensis*]
WP_059956839.1 cytochrome C [*Burkholderia ubonensis*]
WP_059801215.1 cytochrome C [*Burkholderia ubonensis*]
WP_060374144.1 cytochrome C [*Burkholderia ubonensis*]
WP_060228155.1 cytochrome C [*Burkholderia ubonensis*]
WP_060449283.1 cytochrome C [*Burkholderia ubonensis*]
WP_060088315.1 cytochrome C [*Burkholderia ubonensis*]
WP_060141594.1 cytochrome C [*Burkholderia ubonensis*]
WP_059965520.1 cytochrome C [*Burkholderia ubonensis*]
WP_059733305.1 cytochrome C [*Burkholderia ubonensis*]
WP_059849627.1 cytochrome C [*Burkholderia ubonensis*]
WP_060165437.1 cytochrome C [*Burkholderia ubonensis*]
WP_059712923.1 cytochrome C [*Burkholderia ubonensis*]
WP_059737856.1 cytochrome C [*Burkholderia ubonensis*]
WP_059659999.1 cytochrome C [*Burkholderia ubonensis*]
WP_059924960.1 cytochrome C [*Burkholderia ubonensis*]
WP_059777863.1 cytochrome C [*Burkholderia ubonensis*]
WP_060058770.1 cytochrome C [*Burkholderia ubonensis*]
WP_059776014.1 cytochrome C [*Burkholderia ubonensis*]
WP_060123897.1 cytochrome C [*Burkholderia ubonensis*]
WP_060003887.1 cytochrome C [*Burkholderia ubonensis*]
WP_071753220.1 cytochrome C [*Burkholderia ubonensis*]
WP_069271183.1 cytochrome C [*Burkholderia ubonensis*]
WP_060168536.1 cytochrome C [*Burkholderia ubonensis*]
WP_059937950.1 cytochrome C [*Burkholderia ubonensis*]
WP_059651010.1 cytochrome C [*Burkholderia ubonensis*]
WP_059952547.1 cytochrome C [*Burkholderia ubonensis*]
WP_059727989.1 cytochrome C [*Burkholderia ubonensis*]
WP_060328321.1 cytochrome C [*Burkholderia ubonensis*]
WP_059872364.1 cytochrome C [*Burkholderia ubonensis*]
WP_059997503.1 cytochrome C [*Burkholderia ubonensis*]
WP_071773630.1 cytochrome C [*Burkholderia ubonensis*]
WP_059828379.1 cytochrome C [*Burkholderia ubonensis*]
WP_060088886.1 cytochrome C [*Burkholderia ubonensis*]
WP_060248705.1 cytochrome C [*Burkholderia ubonensis*]
WP_036661765.1 cytochrome C [*Pandoraea* sp. SD6-2]
WP_059573013.1 cytochrome C [*Burkholderia* sp. TSV86]
WP_006027348.1 MULTISPECIES: cytochrome C [*Burkholderia*]
WP_069235777.1 cytochrome C [*Burkholderia* sp. Bp7605]
WP_059514380.1 cytochrome C [*Burkholderia* sp. TSV85]
WP_063533919.1 cytochrome C [*Burkholderia* sp. MSMB1589WGS]
WP_059929957.1 MULTISPECIES: cytochrome C [*pseudomallei* group]
WP_060819951.1 cytochrome C [*Burkholderia* sp. BDU19]
WP_059646659.1 MULTISPECIES: cytochrome C [*pseudomallei* group]
WP_038746875.1 cytochrome C [*Burkholderia* sp. ABCPW 111]
WP_059669953.1 cytochrome C [*Burkholderia* sp. MSMB1498]
WP_038801472.1 cytochrome C [*Burkholderia oklahomensis*]
WP_060356553.1 cytochrome C [*Burkholderia* sp. MSMB617WGS]
WP_059582413.1 MULTISPECIES: cytochrome C [*pseudomallei* group]
WP_085508044.1 cytochrome C [*Burkholderia pseudomallei*]
WP_010118598.1 cytochrome C [*Burkholderia oklahomensis*]
WP_059597682.1 cytochrome C [*Burkholderia* sp. BDU6]
WP_025405690.1 cytochrome C [*Burkholderia thailandensis*]
WP_038742304.1 cytochrome C [*Burkholderia pseudomallei*]
WP_009900297.1 cytochrome C [*Burkholderia thailandensis*] (SEQ ID NO:11)
WP_004532924.1 cytochrome C [*Burkholderia pseudomallei*]
WP_058034623.1 cytochrome C [*Burkholderia pseudomallei*]
WP_038758421.1 cytochrome C [*Burkholderia pseudomallei*]
WP_038760788.1 cytochrome C [*Burkholderia pseudomallei*]
WP_004540659.1 cytochrome C [*Burkholderia pseudomallei*]
WP_085547264.1 cytochrome C [*Burkholderia pseudomallei*]
WP_076883397.1 cytochrome C [*Burkholderia pseudomallei*]
WP_059473995.1 cytochrome C [*Burkholderia* sp. BDU5]
WP_041191039.1 cytochrome C [*Burkholderia pseudomallei*]
WP_043296725.1 cytochrome C [*Burkholderia thailandensis*]
WP_063597172.1 cytochrome C [*Burkholderia pseudomallei*]
WP_066496408.1 cytochrome C [*Burkholderia* sp. BDU8]
WP_038799895.1 cytochrome C [*Burkholderia pseudomallei*]
WP_004539114.1 cytochrome C [*Burkholderia pseudomallei*]
WP_004524074.1 cytochrome C [*Burkholderia pseudomallei*]
WP_017881863.1 cytochrome C [*Burkholderia pseudomallei*]

WP_009897184.1 cytochrome C [*Burkholderia thailandensis*]
WP_004536717.1 cytochrome C [*Burkholderia pseudomallei*]
WP_076885712.1 cytochrome C [*Burkholderia pseudomallei*]
WP_066570748.1 cytochrome C [*Burkholderia* sp. ABCPW 14]
WP_076903220.1 cytochrome C [*Burkholderia pseudomallei*]
WP_076936464.1 cytochrome C [*Burkholderia pseudomallei*]
WP_076893617.1 cytochrome C [*Burkholderia pseudomallei*]
WP_043299328.1 cytochrome C [*Burkholderia pseudomallei*]
WP_038785043.1 cytochrome C [*Burkholderia pseudomallei*]
WP_041220968.1 cytochrome C [*Burkholderia pseudomallei*]
WP_076891198.1 cytochrome C [*Burkholderia pseudomallei*]
WP_076883909.1 cytochrome C [*Burkholderia pseudomallei*]
WP_004528232.1 cytochrome C [*Burkholderia pseudomallei*]
WP_085539130.1 cytochrome C [*Burkholderia pseudomallei*]
WP_038784065.1 cytochrome C [*Burkholderia pseudomallei*]
WP_038760183.1 cytochrome C [*Burkholderia pseudomallei*]
WP_038730591.1 cytochrome C [*Burkholderia pseudomallei*]
WP_038765827.1 cytochrome C [*Burkholderia pseudomallei*]
WP_076855330.1 cytochrome C [*Burkholderia pseudomallei*]
WP_004199672.1 cytochrome C [*Burkholderia mallei*]
KGC89207.1 cytochrome C family protein [*Burkholderia pseudomallei*]
ED093432.1 glucose dehydrogenase, beta subunit [*Burkholderia pseudomallei* Pasteur 52237]
WP_011205494.1 cytochrome C subunit II [*Burkholderia pseudomallei*]
KGV82938.1 cytochrome C family protein [*Burkholderia pseudomallei* MSHR4375]
CDU31054.1 putative cytochrome C subunit II [*Burkholderia pseudomallei*]
KGV67566.1 cytochrome C family protein [*Burkholderia pseudomallei* MSHR4299]
EDK84065.1 cytochrome C family protein [*Burkholderia mallei* 2002721280]
WP_074287454.1 cytochrome C [*Burkholderia* sp. GAS332]
WP_035557403.1 cytochrome C [*Burkholderia* sp. 9120]
WP_084534186.1 cytochrome C [*Paraburkholderia dilworthii*]
WP_017774215.1 cytochrome C [*Paraburkholderia kururiensis*]
WP_030100524.1 cytochrome C [*Burkholderia* sp. K24]
WP_028194542.1 cytochrome C [*Paraburkholderia fungorum*]
WP_046573324.1 cytochrome C [*Paraburkholderia fungorum*]
WP_042300635.1 cytochrome C [*Paraburkholderia kururiensis*]
WP_084166897.1 cytochrome C [*Paraburkholderia caledonica*]
SDI05126.1 cytochrome C, mono-and diheme variants [*Paraburkholderia phenazinium*]
WP_051120977.1 cytochrome C [*Paraburkholderia bryophila*]
WP_073428494.1 MULTISPECIES: cytochrome C [*Burkholderiaceae*]
WP_074300113.1 cytochrome C [*Paraburkholderia phenazinium*]
WP_074768708.1 cytochrome C [*Paraburkholderia fungorum*]
WP_075465130.1 cytochrome C [*Ralstonia solanacearum*]
WP_039597687.1 cytochrome C [*Ralstonia* sp. A12]
WP_055334967.1 cytochrome C [*Ralstonia solanacearum*]
WP_078223437.1 cytochrome C [blood disease bacterium A2-HR MARDI]
WP_013213209.1 cytochrome C [*Ralstonia solanacearum*]
WP_063393008.1 cytochrome C [*Ralstonia mannitolilytica*]
WP_003265144.1 cytochrome C, partial [*Ralstonia solanacearum*] (SEQ ID NO:12)
WP_039568931.1 cytochrome C [*Ralstonia solanacearum*]
WP_045786290.1 cytochrome C [*Ralstonia mannitolilytica*]
WP_064802148.1 cytochrome C [*Ralstonia insidiosa*]
WP_021195198.1 MULTISPECIES: cytochrome C [*Ralstonia*]
WP_004629446.1 cytochrome C, mono- and diheme variants family [*Ralstonia pickettii*]
WP_012435095.1 cytochrome C [*Ralstonia pickettii*]
WP_003279246.1 cytochrome C [*Ralstonia solanacearum*]
WP_048931829.1 cytochrome C [*Ralstonia* sp. MD27]
WP_027677928.1 cytochrome C [*Ralstonia* sp. UNC404CL21Col]
WP_012761509.1 cytochrome C [*Ralstonia pickettii*] (SEQ ID NO:13)
WP_045204557.1 cytochrome C [*Burkholderiaceae* bacterium 26]
CUV46938.1 Gluconate 2-dehydrogenase cytochrome C subunit [*Ralstonia solanacearum*]
WP_024973348.1 cytochrome C [*Ralstonia pickettii*]
AKZ27209.1 cytochrome C [*Ralstonia solanacearum*]
WP_020749403.1 oxidoreductase dehydrogenase (cytochrome C subunit) [*Ralstonia solanacearum*]
WP_024976325.1 cytochrome C [*Ralstonia pickettii*]
WP_049842155.1 cytochrome C [*Ralstonia solanacearum*]
WP_028852719.1 cytochrome C [*Ralstonia solanacearum*]
WP_071895582.1 cytochrome C [*Ralstonia solanacearum*]
SFP41323.1 cytochrome C, mono-and diheme variants [*Ralstonia* sp. NFACC01]
WP_064477581.1 cytochrome C [*Ralstonia solanacearum*]
WP_058908222.1 cytochrome C [*Ralstonia solanacearum*]
WP_009238766.1 MULTISPECIES: cytochrome C [*Ralstonia*]
CUV21878.1 Gluconate 2-dehydrogenase cytochrome C subunit [*Ralstonia solanacearum*]
WP_011000726.1 cytochrome C [*Ralstonia solanacearum*]
WP_071507651.1 cytochrome C [*Ralstonia solanacearum*]
WP_065857157.1 cytochrome C [*Ralstonia pickettii*]
WP_019717689.1 cytochrome C [*Ralstonia solanacearum*]
WP_071012822.1 cytochrome C [*Ralstonia solanacearum*]
WP_020831436.1 2-Keto-D-gluconate dehydrogenase [*Ralstonia solanacearum*]
CUV55668.1 Gluconate 2-dehydrogenase cytochrome C subunit [*Ralstonia solanacearum*]

Examples of the mutant cytochrome c protein also include a protein obtained by modifying an amino acid sequence having a sequence identity of not less than 60% to SEQ ID NO:4 such as one described above, for example, the amino acid sequence of any of SEQ ID NO:6 to 13, such that the protein lacks the first and second heme-binding domains as counted from the amino-terminal side. For example, the mutant cytochrome c protein may be the same as any of the amino acid sequences of SEQ ID NOs:6 to 13 except that the protein lacks the first and second heme-binding domains, or may be the same as any of the amino acid sequences of SEQ ID NOs:6 to 13 except that the protein lacks the region comprising the first and second heme-binding domains (the region corresponding to amino acids 43 to 195 of SEQ ID NO:4).

The original sequence to be modified may be the amino acid sequence of each of SEQ ID NOs:6 to 13 having a substitution(s), deletion(s), addition(s), and/or insertion(s) of one or several amino acids in a region(s) other than the modification site (i.e. the site of modification such that the protein lacks the first and second heme-binding domains) and the third heme-binding domain.

Thus, as long as the electron transfer function is maintained, the mutant cytochrome c protein may be a protein having the same amino acid sequence as any of the amino acid sequences of SEQ ID NOs:6 to 13 except that the protein lacks the first and second heme-binding domains and that one or several amino acids are substituted, deleted, added, and/or inserted at a position(s) in a region(s) other than the third heme-binding domain, or may be a protein having the same amino acid sequence as any of the amino acid sequences of SEQ ID NOs:6 to 13 except that the protein lacks the region containing the first and second heme-binding domains (the region corresponding to amino acids 43 to 195 of SEQ ID NO:4) and that one or several amino acids are substituted, deleted, added, and/or inserted at a position(s) in a region(s) other than the third heme-binding domain. The term "one or several" herein means, for example, 1 to 20, 1 to 10, 1 to 8, 1 to 5, or 1 to 3, i.e. 1, 2 or 3. The substitution may be conservative substitution. "Conservative substitution" means substitution between amino acids having similar properties, such as substitution between acidic amino acids, substitution between neutral amino acids, or substitution between basic amino acids.

<Oxidoreductase-Cytochrome Complex>

The mutant cytochrome protein according to one embodiment of the present invention may be used together with a catalytic subunit of an oxidoreductase, and is capable of receiving an electron generated by oxidation-reduction reaction and then transferring the electron to an electrode. Thus, an oxidoreductase-cytochrome complex containing the mutant cytochrome protein can be used as an electrochemical sensor. The electrochemical sensor may be a glucose sensor containing the mutant cytochrome protein and glucose oxidoreductase.

<Oxidoreductase>

The oxidoreductase is not limited as long as it is an enzyme capable of oxidation-reduction of a measurement target substance. Examples of its catalytic subunit include catalytic subunits of enzymes containing at least one of pyrrolo-quinoline quinone (PQQ) and flavin adenine dinucleotide (FAD). Examples of an oxidoreductase containing PQQ include PQQ glucose dehydrogenase (PQQGDH), and examples of an oxidoreductase containing FAD include cytochrome glucose dehydrogenase (CyGDH) having an α-subunit containing FAD and glucose oxidase (GOD). Other examples of the oxidoreductase include cholesterol oxidase, quinoheme ethanol dehydrogenase (QHEDH, PQQ Ethanol dh), sorbitol dehydrogenase (Sorbitol DH), D-fructose dehydrogenase (Fructose DH), cellobiose dehydrogenase, and lactate dehydrogenase.

Among these, glucose dehydrogenase (GDH) is preferred.

The glucose dehydrogenase is not limited as long as it has the glucose dehydrogenase activity. Glucose dehydrogenase catalytic subunits derived from various organisms, including those already known, may be used. It may be derived from the same microorganism as the microorganism from which the mutant cytochrome protein is derived. More specifically, for example, an α-subunit protein derived from the *Burkholderia cepacia* KS1 strain having the amino acid sequence of SEQ ID NO:3 may be used. However, as long as the subunit can function as an α-subunit of GDH, it may be a protein having the same amino acid sequence as the amino acid sequence of SEQ ID NO:3 except that one or several amino acid residues are substituted, deleted, inserted, and/or added. Further, as long as the subunit can function as an α-subunit of GDH, it may be a protein having the same amino acid sequence as the amino acid sequence of an α-subunit of a strain other than the KS1 strain except that one or several amino acid residues are substituted, deleted, inserted, and/or added. The term "one or several" means, for example, 1 to 20, 1 to 10, or 1 to 5, i.e. 1, 2, 3, 4 or 5. A number of mutations are known to increase the enzymatic activity or the substrate specificity of the α-subunit protein of glucose dehydrogenase. α-Subunit proteins of glucose dehydrogenase having such mutations may be used.

The glucose dehydrogenase complex may further contain a γ-subunit in addition to the mutant cytochrome protein and the catalytic subunit. The γ-subunit is not limited as long as it functions as a γ-subunit, and γ-subunits derived from various organisms, including those already known, may be used. It may be derived from the same microorganism as the microorganism from which the mutant cytochrome protein is derived. More specifically, for example, a protein derived from the *Burkholderia cepacia* KS1 strain having the amino acid sequence of SEQ ID NO:2 may be used. However, as long as the subunit can function as a γ-subunit, it may be a protein having the same amino acid sequence as the amino acid sequence of SEQ ID NO:2 except that one or several amino acid residues are substituted, deleted, inserted, and/or added. Further, as long as the subunit can function as a γ-subunit, it may be a protein having the same amino acid sequence as the amino acid sequence of a γ-subunit of a strain other than the KS1 strain except that one or several amino acid residues are substituted, deleted, inserted, and/or added. The term "one or several" means, for example, 1 to 15, 1 to 10, or 1 to 5, i.e. 1, 2, 3, 4 or 5. Alternatively described, as long as the subunit can function as a γ-subunit, it may be a protein having an amino acid identity of not less than 60%, preferably not less than 80%, more preferably not less than 90% or 95% to SEQ ID NO:2. The term "functions as a γ-subunit" means that, when a complex is formed together with an α-subunit(s), the γ-subunit has a function to increase the GDH activity of the complex.

<DNA>

The present invention also provides a DNA encoding the mutant cytochrome protein. The nucleotide sequence of the DNA encoding the mutant cytochrome protein can be specified based on the amino acid sequence of the mutant cytochrome protein. For example, the DNA can be obtained by modifying the nucleotide sequence of a DNA encoding a wild-type cytochrome protein such that the protein lacks the first and second heme-binding domains or a region(s) containing these.

Specific examples of the DNA encoding a cytochrome protein of *Burkholderia cepacia* include a DNA containing the nucleotide sequence of nucleotides 2386 to 3660 of SEQ ID NO:1, which encodes a β-subunit of glucose dehydrogenase. The DNA encoding a β-subunit is not limited to the DNA having the nucleotide sequence of nucleotides 2386 to 3660 of SEQ ID NO:1, and may be a DNA which hybridizes, under stringent conditions, with the DNA having the complementary sequence of this nucleotide sequence, and which encodes a protein that can function as a β-subunit.

Examples of the DNA encoding the mutant cytochrome protein include the DNA consisting of the nucleotide sequence of nucleotides 3372 to 3660 or 3325 to 3660 of SEQ ID NO:5, and a DNA which hybridizes, under stringent conditions, with the DNA having the complementary sequence of this nucleotide sequence, and which encodes a protein that can function as the mutant cytochrome protein.

A mutant cytochrome protein having a desired mutation can be obtained by constructing a mutant DNA by, for example, introduction of a desired amino acid deletion(s) to a DNA encoding a cytochrome protein by site-directed mutagenesis, or amplification of only a particular region of the DNA by PCR, and then allowing expression from the mutant DNA using an appropriate expression system.

In cases where an oxidoreductase-cytochrome complex containing the mutant cytochrome protein is used, it is preferred to use a DNA encoding the catalytic subunit of the oxidoreductase together with a DNA encoding the mutant cytochrome protein.

The DNA encoding the catalytic subunit of the oxidoreductase is not limited, and may be appropriately selected and used depending on the purpose. Examples of the DNA include a DNA encoding a glucose dehydrogenase α-subunit having the nucleotide sequence of nucleotides 764 to 2380 of SEQ ID NO:1. The α-subunit gene may be a DNA which hybridizes, under stringent conditions, with the DNA having the complementary sequence of the nucleotide sequence of nucleotides 764 to 2380 of the nucleotide sequence of SEQ ID NO:1, and which encodes a protein having the GDH activity.

In cases where a glucose dehydrogenase γ-subunit is contained in the oxidoreductase-cytochrome complex, it is preferred to use a DNA encoding the γ-subunit of the oxidoreductase together with a DNA encoding the mutant cytochrome protein and a DNA encoding the catalytic subunit.

Specific examples of the DNA encoding the γ-subunit include a DNA containing the nucleotide sequence of nucleotides 258 to 761 of SEQ ID NO:1. The DNA encoding the γ-subunit may be a DNA which hybridizes, under stringent conditions, with the DNA having the complementary sequence of the nucleotide sequence of nucleotides 258 to 761 of SEQ ID NO:1, and which encodes a protein that can function as a γ-subunit.

Examples of the stringent conditions described above include conditions that allow hybridization of DNAs having an identity of not less than 80%, not less than 90%, or not less than 95%, with each other. Specific examples of the stringent conditions include those in which hybridization reaction is followed by washing with 0.1×SSC and 0.1% SDS at 60° C. Alternatively, preferred DNA has the above described sequence identity to the parent DNA, i.e. to the DNA to which hybridization was contemplated.

The DNA encoding the cytochrome protein, the DNA encoding the catalytic subunit of oxidoreductase, and the like can be obtained by, for example, using chromosomal DNA of a microorganism such as *Burkholderia cepacia* as a template for PCR or for the hybridization method.

The nucleotide sequence of a chromosomal DNA fragment containing the GDH γ-subunit gene, α-subunit gene, and β-subunit gene of the *Burkholderia cepacia* KS1 strain is shown in SEQ ID NO:1. This nucleotide sequence has three open reading frames (ORFs). As counted from the 5'-end side, the first ORF encodes the γ-subunit (SEQ ID NO:2); the second ORF encodes the α-subunit (SEQ ID NO:3); and the third ORF encodes the β-subunit (SEQ ID NO:4).

The mutant cytochrome protein and the catalytic subunit may be separately expressed from their DNAs, or may be expressed using a DNA that polycistronically contains the DNA encoding the mutant cytochrome protein and the DNA encoding the catalytic subunit.

<Vector>

The vector used for obtaining the genes of the mutant cytochrome protein and the catalytic subunit, introducing the mutations, expressing the genes, and the like is not limited as long as the vector can function in the host microorganism. Examples of the vector include those that can function in bacteria belonging to the genus *Escherichia*, such as pTrc99A, pBR322, pUC18, pUC118, pUC19, pUC119, pACYC184, and pBBR122. The promoter to be used for the gene expression may also be appropriately selected depending on the host. Examples of the promoter include lac, trp, tac, trc, PL, tet, and PhoA.

<Transformant>

By introducing the DNA described above or a vector containing it into a host microorganism to obtain a transformant, the mutant cytochrome protein or the oxidoreductase-cytochrome complex can be expressed. For the transformation, a known method may be employed. Examples of the method include the competent cell method by calcium treatment, the protoplast method, and the electroporation method.

The host microorganism is not limited as long as it can be used for protein expression. Examples of the host microorganism include, but are not limited to, bacteria belonging to the genus *Escherichia* such as *Escherichia coli*; bacteria belonging to the genus *Bacillus* such as *Bacillus subtilis*; yeasts such as *Saccharomyces cerevisiae* and *Pichia pastoris*; and filamentous fungi such as *Aspergillus niger* and *Aspergillus oryzae*.

<Biosensor>

The mutant cytochrome protein according to one embodiment of the present invention can be used for an electrochemical biosensor that utilizes oxidation-reduction reaction. Regarding the type of the biosensor, the biosensor may be used for a variety of uses depending on the type of the oxidoreductase used in combination. For example, in cases where glucose oxidoreductase is used as the oxidoreductase, a glucose sensor may be provided. In cases where lactate dehydrogenase is used as the oxidoreductase, a lactate sensor may be provided.

Among these, a glucose sensor is preferred. In cases where a glucose sensor is prepared, the mutant cytochrome protein and a catalytic subunit of the oxidoreductase may be contained in the reagent layer of the enzyme electrode. Further, a γ-subunit may be contained. By this, glucose in the sample can be oxidized by the catalytic subunit. The electron generated thereby is accepted by the mutant cytochrome protein and then transferred to the electrode. As a result, a response current depending on the glucose concentration in the sample flows, and the glucose concentration can then be calculated based on the current value.

Specific examples of the glucose sensor include glucose sensors that use, as a working electrode, an enzyme electrode formed by immobilization of a complex containing the mutant cytochrome protein and a catalytic subunit of glucose dehydrogenase on a surface of an electrode such as a gold electrode, platinum electrode, or carbon electrode. The sensor means a measurement system for electrochemically measuring the concentration of a test substance of interest, and may be a system containing the following three electrodes: a working electrode (enzyme electrode), a counter electrode (platinum or the like), and a reference electrode (Ag/AgCl or the like). The sensor may also be a two-electrode system constituted by a working electrode and a counter electrode, such as those used in conventional, simple blood glucose level systems. The sensor may further contain a constant-temperature cell in which a buffer and a test sample are to be placed; a power source for applying an electric potential to the working electrode; an ammeter; a recorder; and/or the like. The sensor may be either a batch-type sensor or a flow-type sensor. The flow-type sensor may be a sensor which can continuously measure the blood glucose level. That is, the sensor may be a sensor having a two-electrode system or a three-electrode system on which the enzyme containing the mutant cytochrome protein is immobilized, which electrode system is inserted into a blood sample or a dialysis sample that is continuously supplied, or into blood or interstitial fluid, to perform the measurement. The structure of such an enzyme sensor is well known in the art, and described in, for example, Biosensors—Fundamental and Applications—Anthony P. F. Turner, Isao Karube and Geroge S. Wilson, Oxford University Press 1987.

The measurement of the glucose concentration using the glucose sensor according to one embodiment of the present invention can be carried out, for example, as follows. A buffer is placed in a constant-temperature cell of the sensor, and the temperature of the cell is kept constant. As a working electrode, an enzyme electrode on which the mutant cytochrome protein and a catalytic subunit protein of glucose oxidoreductase are immobilized is used. As a counter electrode, for example, a platinum electrode is used. As a reference electrode, for example, an Ag/AgCl electrode is used. A constant electric potential is applied to the working electrode (for example, by application of 0 to +300 mV, 0 to +150 mV, or 0 to +100 mV with respect to a silver-silver chloride electrode). After the electric current becomes constant, a sample containing glucose is placed in the constant-temperature cell, and the increase in the electric current is measured. According to a calibration curve prepared using glucose solutions having standard concentrations, the glucose concentration in the sample can be calculated.

A GDH complex containing the mutant cytochrome protein and a GDH catalytic subunit can also be used as a component of a glucose assay kit. The glucose assay kit may contain a coloring or luminescence reagent, a dilution buffer, a standard substance, manufacturer's instructions, and/or the like in addition to the GDH complex containing the mutant cytochrome protein and a GDH catalytic subunit.

For example, a glucose sensor and a glucose assay kit using the wild-type GDH of *Burkholderia cepacia* are described in US 2004/0023330 A1. The GDH containing the mutant cytochrome protein can be similarly used.

EXAMPLES

More concrete embodiments of the present invention are described below by referring to Examples. However, embodiments of the present invention are not limited to these Examples.

[Example 1] Construction of Mutant GDH β-Subunit Gene

As a plasmid to be used for construction of a mutant GDH β-subunit gene, pTrc99Aγα(QYY)β, which was prepared by introducing mutations to the α-subunit in the plasmid pTrc99Aγαβ described in JP 2012-090563 A, was used. This plasmid is a plasmid prepared by inserting a DNA fragment containing in frame the GDH γ-subunit structural gene, the α-subunit structural gene, and the β-subunit structural gene isolated from chromosomal DNA of the *Burkholderia cepacia* KS1 strain (FERM BP-7306) into the cloning site of the pTrc99A vector, wherein in the α-subunit structural gene, the codons encoding the serine at the 326th residue, the serine at the 365th residue, and the alanine at the 472nd residue are substituted with codons encoding glutamine, tyrosine, and tyrosine, respectively. The structural genes of GDH in this plasmid are regulated by the trc promoter. pTrc99Aγαβ has an ampicillin resistance gene.

First, using the plasmid DNA described above as a template, and the oligonucleotides having the following sequences as primers, PCR was carried out to amplify a DNA fragment encoding the γ-subunit, the α-subunit, and the signal sequence of the β-subunit of GDH.

```
[Forward primer]
                                       (SEQ ID NO: 14)
5'-ACGTAGCCATGGCACACAACGACAACCACTC-3'

[Reverse primer]
                                       (SEQ ID NO: 15)
5'-ATCGGCCGCGCGCGCGAAGCCCGGCAA-3'
```

The PCR was carried out using the reaction composition shown below by incubation at 95° C. for 30 seconds, 25 cycles of incubation at 95° C. for 30 seconds, at 55° C. for 1 minute, and then at 72° C. for 2 minutes, and then incubation at 72° C. for 5 minutes, followed by keeping the reaction liquid at 4° C.

[Reaction Liquid Composition]
 pTrc99Aγα(QYY)β (100 ng/μl) 0.5 μl
 10× Reaction buffer 2 μl
 Forward primer (100 ng/μl) 0.5 μl
 Reverse primer (100 ng/μl) 0.5 μl
 dNTP 0.4 μl
 Distilled water 15.7 μl
 DNA polymerase 0.4 μl
 Total 20 μl Further, DNA fragments encoding the third heme-binding domain of the β-subunit, that is, the region of amino acids 314 to 425 or 330 to 425 of SEQ ID NO:4, were amplified by PCR using the oligonucleotides having the sequences shown below as primers. Each of the forward primers has a sequence corresponding to the signal sequence of the β-subunit at its 5'-end side.

```
[Forward primer for amplification of the region
from 314 to 425]
                                       (SEQ ID NO: 16)
5'-TTGCCGGGCTTCGCGCGCGCGGCCGATCTGCGCGGTGTCGCGCTC

GCG-3'

[Forward primer for amplification of the region
from 330 to 425]
                                       (SEQ ID NO: 17)
5'-TTGCCGGGCTTCGCGCGCGCGGCCGATTATCTCGGCAACTGCGCG

ACG-3'

[Reverse Primer]
                                       (SEQ ID NO: 18)
5'-GTGGTGCTCGAGTGCGGCCGCGCGCAGCTTCGCGACGTCCTG-3'
```

The PCR was carried out using the reaction composition shown below by incubation at 95° C. for 30 seconds, 25 cycles of incubation at 95° C. for 30 seconds, at 55° C. for 1 minute, and then at 72° C. for 30 seconds, and then incubation at 72° C. for 5 minutes, followed by keeping the reaction liquid at 4° C.

[Reaction Liquid Composition]

pTrc99Aγα(QYY)β (100 ng/μl) 0.5 μl
10× Reaction buffer 2 μl
Forward primer (100 ng/μl) 0.5 μl
Reverse primer (100 ng/μl) 0.5 μl
dNTP 0.4 μl
Distilled water 15.7 μl
DNA polymerase 0.4 μl
Total 20 μl The DNA fragments obtained by the above operations were separately purified and then mixed together to provide a template, which was used to perform overlap extention PCR using the oligonucleotides having the sequences shown below as primers, thereby linking and amplifying the DNA fragments. The reverse primer was designed to have a histidine tag sequence such that a histidine tag is added to the C-terminus of the mutant β-subunit.

[Forward primer]
(SEQ ID NO: 14)
5'-ACGTAGCCATGGCACACAACGACAACCACTC-3'

[Reverse primer]
(SEQ ID NO: 19)
5'-GTACGTAAGCTTTCAGTGGTGGTGGTGGTGC
TCGAGTGCGGCCGC-3'

The PCR was carried out using the reaction composition shown below by incubation at 95° C. for 30 seconds, 25 cycles of incubation at 95° C. for 30 seconds, at 55° C. for 1 minute, and then at 72° C. for 4 minutes, and then incubation at 72° C. for 5 minutes, followed by keeping the reaction liquid at 4° C.

[Reaction Liquid Composition]

PCR product of the region from the γ-subunit to the β-subunit signal sequence (100 ng/μl) 1 μl
PCR product of the β-subunit 314 to 425 or PCR product of the β-subunit 330 to 425 (100 ng/μl) 1 μl
10× Reaction buffer 2 μl
Forward primer (100 ng/μl) 0.5 μl
Reverse primer (100 ng/μl) 0.5 μl
dNTP 0.4 μl
Distilled water 14.2 μl
DNA polymerase 0.4 μl
Total 20 μl After purification of the PCR product obtained, the N-terminal side was digested with NcoI, and the C-terminal side was digested with HindIII, followed by ligating the digestion product into pTrc99A which had been treated with the same enzymes. Escherichia coli DH5α was transformed with the obtained recombinant vector. Colonies formed on LB agar medium supplemented with 50 μg/mL carbenicillin were collected. The transformants obtained were cultured in liquid LB medium, and plasmids were extracted therefrom. Thereafter, the DNA fragments inserted therein were analyzed. As a result, insertion of the sequence covering γ-subunit, the α-subunit, and the signal sequence of the β-subunit, as well as the gene encoding the 314th to 425th residues of the β-subunit or the gene encoding the 330th to 425th residues of the β-subunit, was confirmed. These plasmids were designated pTrc99Aγα(QYY)β314-His and pTrc99Aγα(QYY)β330-His, respectively. The structural genes of GDH in these plasmids have a histidine tag at the C-terminus of the β-subunit, and are regulated by the trc promoter. Each plasmid has an ampicillin resistance gene.

[Example 2] Expression of Burkholderia cepacia GDH Containing Mutant GDH Subunit A GDH containing a mutant GDH β-subunit gene was produced using the expression plasmid obtained in Example 1.

The Escherichia coli BL21 (DE3) strain to which the GDH expression plasmid containing the mutant GDH β-subunit gene and the plasmid pBBJMccm having genes indispensable for maturation of cytochrome c were introduced was cultured in 3 ml of LB medium (supplemented with 50 μg/ml carbenicillin and 50 μg/ml kanamycin) with shaking at 37° C. overnight using a test tube. The resulting culture liquid was inoculated at 1% to two 300-ml Sakaguchi flasks each containing 50 ml of a medium prepared such that the composition per 1 L of the culture liquid was as shown in Table 1 (supplemented with 50 μg/ml carbenicillin and 50 μg/ml kanamycin), and shake culture was carried out at 25° C. for 28 hours.

However, in cases where the host can constantly allow maturation of cytochrome c, for example, in cases where the transformant has the ccm gene inserted into the genome by homologous recombination or the like and is constantly expressing it, vectors such as pBBJMccm are not necessary.

TABLE 1

| Medium Composition (per 1 L) | |
|---|---|
| Tryptone | 10 g |
| Yeast extract | 5 g |
| Sodium chloride | 5 g |
| Glycerin | 0.5 g |
| Glucose | 0.05 g |
| Lactose monohydrate | 0.21 g |
| Ammonium sulfate | 0.33 g |
| Potassium dihydrogen phosphate | 0.68 g |
| Disodium hydrogen phosphate dodecahydrate | 1.79 g |
| Magnesium sulfate | 0.025 g |

The bacterial cells were collected from the culture liquid obtained by the culture described above, and BugBuster Protein Extraction reagent (Merck Millipore) was added thereto at 5 ml per 1 g of the wet bacterial cells obtained, followed by suspending and lysing the bacterial cells. The resulting suspension was centrifuged (15,000 rpm, 20 minutes, 4° C.), and then the residue was discarded to provide a crude enzyme sample.

Regarding γα(QYY)β314-His, the crude enzyme sample was dialyzed overnight against 20 mM sodium phosphate buffer (pH 7.0) supplemented with 0.5 M sodium chloride and 20 mM imidazole, and then added to a column packed with Ni-NTA agarose (QIAGEN) equilibrated with the same buffer. After washing with 20 mM sodium phosphate buffer (pH 7.0) supplemented with 0.5 M sodium chloride and 54 mM imidazole, the sample was eluted with 20 mM sodium phosphate buffer (pH 7.0) supplemented with 0.5 M sodium chloride and 140 mM imidazole, to obtain a purified enzyme sample.

[Example 3] Functional Analysis of Burkholderia cepacia GDH Containing Mutant GDH β-Subunit Measurement of the GDH activity was carried out by the PMS/DCIP system and the ruthenium (Ru)/MTT system. The former system shows the general GDH activity, and the latter system shows the GDH activity based on the electron transfer to a mediator through the β-subunit.

The activity measurement in the PMS/DCIP system was carried out as follows. To 20 mM potassium phosphate buffer (pH 7.0), an enzyme sample, methylphenazine methosulfate (PMS) (final concentration, 0.6 mM), 2,6-dichlorophenol indophenol (DCIP) (final concentration, 0.06 mM), and glucose (final concentration, 4 mM or 40 mM) were added, and the degree of change in the absorbance at 600 nm, which is the absorption wavelength derived from DCIP, per 1 minute was measured using a spectrophotometer.

The activity measurement in the Ru/MTT system was carried out as follows. To 20 mM potassium phosphate buffer (pH 7.0), an enzyme sample, hexaammineruthenium (III) chloride (final concentration, 2%), 3-(4,5-dimethyl-2-thiazolyl)-2,5-diphenyl-2H-tetrazolium bromide (MTT) (final concentration, 1 mM), and glucose (final concentration, 4 mM or 40 mM) were added, and the amount of change in the absorbance at 565 nm, which is the absorption wavelength derived from formazan produced from MTT, per 1 minute was measured using a spectrophotometer.

The results of activity measurement of the crude enzyme samples are shown in Table 2.

TABLE 2

| | | Enzyme activity (U/mg) at each substrate concentration | | | |
|---|---|---|---|---|---|
| | | PMS/DCIP | | Ru/MTT | |
| | mg/ml | 4 mM Glc | 40 mM Glc | 4 mM Glc | 40 mM Glc |
| γα(QYY)β-His | 7.00 | 5.35 | 19.28 | 1.21 | 3.24 |
| γα(QYY)β314-His | 5.08 | 5.40 | 12.01 | 0.14 | 0.20 |
| γα(QYY)β330-His | 4.03 | 4.18 | 10.0 | 0.11 | 0.11 |

As shown in Table 2, both mutants exhibited the GDH activity in the Ru/MTT system although the activity was lower than that of the enzyme containing the wild-type β-subunit. Thus, it was suggested that these mutants are capable of electron transfer to the mediator through the β-subunit. In wild-type enzyme, a γα complex containing no β-subunit showed an enzyme activity of about 45 U/mg when PMS/DCIP was used as an electron acceptor (Biochimica et Biophysica Acta, 1645(2), 133-138). This corresponded to only about 15% of enzyme activity as compared to the value observed for the complex containing the β-subunit (about 300 U/mg; Journal of Biotechnology, 123(2), 127-136). In contrast, each complex containing a mutant cytochrome c protein showed almost the same activity as that observed for the complex containing the wild-type β-subunit. It was thus found that the mutant β-subunit receives an electron from the α-subunit, and then transfers the electron to PMS/DCIP.

γα(QYY)β314 was purified, and its enzyme activity for 40 mM glucose was measured according to the procedure described above. The measurement was also carried out for γα(QYY)β separately prepared, which contains the wild-type β-subunit. The results are shown in Table 3.

TABLE 3

| | | Enzyme activity (U/mg) | |
|---|---|---|---|
| | mg/ml | PMS/DCIP | Ru/MTT |
| γαQYYβ-His | 7.79 | 644.3 | 55.0 |
| γα(QYY)β314-His | 8.69 | 154.0 | 18.7 |

The purified γα(QYY)β314 showed the GDH activity in the Ru/MTT system, and its ratio to the GDH activity in the PMS/DCIP system was similar to that in the case of the enzyme complex containing the wild-type β-subunit. It was thus suggested that this mutant allows electron transfer to the mediator through the truncated β-subunit similarly to the enzyme complex containing the wild-type β-subunit.

[Example 4] Preparation of Glucose Sensor

An enzyme electrode in which GDH containing a mutant β-subunit is immobilized on a gold surface through a monolayer-forming molecule was prepared. As the monolayer-forming molecule, DSH, which is as shown below, was used.

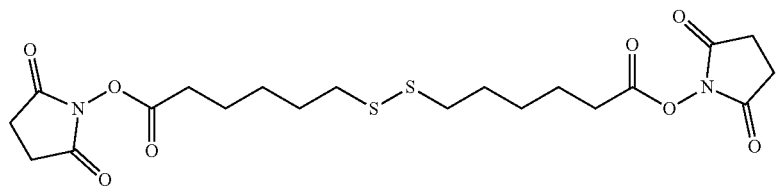

Dithiobis (succinimidyl hexanoate): DSH

More specifically, a gold wire (diameter, 0.5 mm; length, 6 to 7 cm) was immersed in Piranha solution (200 µl) at room temperature for 2 hours, and then washed with acetone. The gold wire was then immersed in a solution of DSH in acetone (concentration, 20 µM), and incubated at 25° C. for 24 hours to allow binding of thiol groups of DSH to the gold surface. Subsequently, the gold wire was washed with acetone, and then immersed in phosphate buffer (300 µl) containing the GDH α, β-subunit complex (concentration, 0.03 mg/ml), followed by incubation at 4° C. overnight to allow binding of the enzyme complex through a functional group of DSH, thereby obtaining an enzyme electrode.

[Example 5] Measurement of Glucose Concentration

Using the enzyme electrode described above, the response current value for 0 mM (background), 1 mM, 5 mM, or 50 mM aqueous glucose solution was measured by chronoamperometry. The glucose measurement was carried out at 37° C. using a counter electrode (Pt wire) and a reference electrode (silver/silver chloride) by application of an electric potential of 0 V, +0.1 V, or +0.4 V (vs. silver/silver chloride) to the working electrode.

<Results>

Using as a reference the glucose concentration properties of the current value obtained by the application of 400 mV with respect to the silver-silver chloride electrode, the current values at 0 mV and 100 mV were compared.

As a result, as shown in FIG. 1, in the case of application of an electric potential of 0 mV, the Comparative Example (dotted line, glucose sensor containing a glucose dehydrogenase (GDH) complex having a wild-type β-subunit) did not show an oxidation current dependent on the glucose concentration, but the Example (solid line) showed an oxidation current dependent on the glucose concentration.

In the case of application of an electric potential of 100 mV, the Comparative Example also showed an oxidation current dependent on the glucose concentration, but the Example showed a higher electric current value output.

It was thus shown that the sensor using the truncated β-subunit in the Example enables acquisition of the catalytic electric current even at a lower oxidation potential compared to the sensor using the wild-type β-subunit.

INDUSTRIAL APPLICABILITY

The biosensor using the mutant cytochrome protein according to one embodiment of the present invention is capable of measuring the electric current at a low electric potential, and may be used for biosensors such as glucose sensors.

While the invention has been described in detail with reference to exemplary embodiments thereof, it will be apparent to one skilled in the art that various changes may be made, and equivalents employed, without departing from the scope of the invention. Each of the aforementioned documents as well as JP2017-131345 is incorporated by reference herein in its entirety.

What is claimed is:

1. A DNA encoding a mutant cytochrome protein originated from a wild-type cytochrome protein having three heme-binding domains, the mutant cytochrome protein lacking the first heme-binding domain and the second heme-binding domain as counted from the N-terminus,
wherein the mutant cytochrome protein is capable of electron transfer at a low electric potential compared to the wild-type cytochrome protein having three heme-binding domains, and
said mutant cytochrome protein consists of an amino acid sequence selected from the group consisting of:
a) the amino acid sequence of amino acids 314 to 425 of SEQ ID NO:4,
b) the amino acid sequence of amino acids 330 to 425 of SEQ ID NO:4,
c) an amino acid sequence which is at least 80% identical to the amino acid sequence of amino acids 314 to 425 of SEQ ID NO:4 with the proviso that the third heme-binding domain of amino acids 334 to 338 is maintained, and
d) an amino acid sequence which is at least 80% identical to the amino acid sequence of amino acids 330 to 425 of SEQ ID NO:4 with the proviso that the third heme-binding domain of amino acids 334 to 338 is maintained.

2. The DNA according to claim 1, wherein said mutant cytochrome protein consists of c) the amino acid sequence which is at least 80% identical to the amino acid sequence of amino acids 314 to 425 of SEQ ID NO:4 with the proviso that the third heme-binding domain of amino acids 334 to 338 is maintained.

3. The DNA according to claim 1, wherein said mutant cytochrome protein consists of d) the amino acid sequence which is at least 80% identical to the amino acid sequence of amino acids 330 to 425 of SEQ ID NO:4 with the proviso that the third heme-binding domain of amino acids 334 to 338 is maintained.

4. The DNA according to claim 1, wherein said mutant cytochrome protein lacks a region(s) comprising the first and second heme-binding domains.

5. The DNA according to claim 4, wherein the region comprising the first and second heme-binding domains corresponds to the region of amino acids from 43 to 195 of SEQ ID NO:4.

6. The DNA according to claim 1, wherein the cytochrome protein having three heme-binding domains is a cytochrome c protein.

7. The DNA according to claim 6, wherein the cytochrome c protein is that of a *Burkholderia* microorganism.

8. The DNA according to claim 7, wherein the cytochrome c protein is that of *Burkholderia cepacia*.

9. The DNA according to claim 1, wherein the original cytochrome protein having three heme-binding domains comprises an amino acid sequence which is at least 60% identical to SEQ ID NO: 4.

10. A DNA encoding a mutant cytochrome protein originated from a wild-type cytochrome protein having three heme-binding domains, the mutant cytochrome protein lacking the first heme-binding domain and the second heme-binding domain as counted from the N-terminus,
wherein the mutant cytochrome protein is capable of electron transfer at a low electric potential compared to the wild-type cytochrome protein having three heme-binding domains, and
wherein said mutant cytochrome protein consists of the amino acid sequence selected from the group consisting of:
a) the amino acid sequence of amino acids 314 to 425 of SEQ ID NO:4,
b) the amino acid sequence of amino acids 330 to 425 of SEQ ID NO:4,
c) an amino acid sequence which is the same as the amino acid sequence of amino acids 314 to 425 of SEQ ID NO:4 except that one to twenty amino acids are substituted, deleted, inserted, and/or added with the proviso that the third heme-binding domain of amino acids 334 to 338 is maintained, and
d) an amino acid sequence which is the same as the amino acid sequence of amino acids 330 to 425 of SEQ ID NO:4 except that one to twenty amino acids are substituted, deleted, inserted, and/or added with the proviso that the third heme-binding domain of amino acids 334 to 338 is maintained.

11. A recombinant vector comprising the DNA according to claim 1.

12. A cell transformed with the recombinant vector according to claim 11.

13. The DNA according to claim 1, wherein the mutant cytochrome protein consists of the amino acid sequence of amino acids 314 to 425 of SEQ ID NO:4.

14. The DNA according to claim 1, wherein the mutant cytochrome protein consists of the amino acid sequence of amino acids 330 to 425 of SEQ ID NO:4.

15. The DNA according to claim 10, wherein mutant cytochrome protein consists of the amino acid sequence which is the same as the amino acid sequence of amino acids 314 to 425 of SEQ ID NO:4 except that one to twenty amino acids are substituted, deleted, inserted, and/or added with the proviso that the third heme-binding domain of amino acids 334 to 338 is maintained.

16. The DNA according to claim 10, wherein mutant cytochrome protein consists of the amino acid sequence which is the same as the amino acid sequence of amino acids 330 to 425 of SEQ ID NO:4 except that one to twenty amino acids are substituted, deleted, inserted, and/or added with the proviso that the third heme-binding domain of amino acids 334 to 338 is maintained.

17. The DNA according to claim 1, wherein mutant cytochrome protein consists of the amino acid sequence which is at least 90% identical to the amino acid sequence of amino acids 314 to 425 of SEQ ID NO:4 with the proviso that the third heme-binding domain of amino acids 334 to 338 is maintained.

18. The DNA according to claim 1, wherein mutant cytochrome protein consists of the amino acid sequence which is at least 90% identical to the amino acid sequence of amino acids 330 to 425 of SEQ ID NO:4 with the proviso that the third heme-binding domain of amino acids 334 to 338 is maintained.

* * * * *

SEQUENCE LISTING

```
<160> NUMBER OF SEQ ID NOS: 19

<210> SEQ ID NO 1
<211> LENGTH: 3706
<212> TYPE: DNA
<213> ORGANISM: Burkholderia cepacia
<220> FEATURE:
<221> NAME/KEY: CDS
<222> LOCATION: (258)..(761)
<220> FEATURE:
<221> NAME/KEY: CDS
<222> LOCATION: (764)..(2380)
<220> FEATURE:
<221> NAME/KEY: CDS
<222> LOCATION: (2386)..(3660)

<400> SEQUENCE: 1
aagctttctg tttgattgca cgcgattcta accgagcgtc tgtgaggcgg aacgcgacat      60
gcttcgtgtc gcacacgtgt cgcgccgacg acacaaaaat gcagcgaaat ggctgatcgt     120
tacgaatggc tgacacattg aatggactat aaaaccattg tccgttccgg aatgtgcgcg     180
tacatttcag gtccgcgccg atttttgaga aatatcaagc gtggttttcc cgaatccggt     240
gttcgagaga aggaaac atg cac aac gac aac act ccc cac tcg cgt cgc        290
                   Met His Asn Asp Asn Thr Pro His Ser Arg Arg
                    1               5                   10 cac ggc gac gca gcc gca tca ggc atc acg cgg cgt caa tgg ttg caa       338
His Gly Asp Ala Ala Ala Ser Gly Ile Thr Arg Arg Gln Trp Leu Gln
            15                  20                  25 ggc gcg ctg gcg ctg acc gca gcg ggc ctc acg ggt tcg ctg aca ttg       386
Gly Ala Leu Ala Leu Thr Ala Ala Gly Leu Thr Gly Ser Leu Thr Leu
        30                  35                  40 cgg gcg ctt gca gac aac ccc ggc act gcg ccg ctc gat acg ttc atg       434
Arg Ala Leu Ala Asp Asn Pro Gly Thr Ala Pro Leu Asp Thr Phe Met
    45                  50                  55 acg ctt tcc gaa tcg ctg acc ggc aag aaa ggg ctc agc cgc gtg atc       482
Thr Leu Ser Glu Ser Leu Thr Gly Lys Lys Gly Leu Ser Arg Val Ile
60                  65                  70                  75 ggc gag cgc ctg ctg cag gcg ctg cag aag ggc tcg ttc aag acg gcc       530
Gly Glu Arg Leu Leu Gln Ala Leu Gln Lys Gly Ser Phe Lys Thr Ala
                80                  85                  90 gac agc ctg ccg cag ctc gcc ggc gcg ctc gcg tcc ggt tcg ctg acg       578
```

```
                Asp Ser Leu Pro Gln Leu Ala Gly Ala Leu Ala Ser Gly Ser Leu Thr
                            95                  100                 105 cct gaa cag gaa tcg ctc gca ctg acg atc ctc gag gcc tgg tat ctc        626
Pro Glu Gln Glu Ser Leu Ala Leu Thr Ile Leu Glu Ala Trp Tyr Leu
            110                 115                 120 ggc atc gtc gac aac gtc gtg att acg tac gag gaa gca tta atg ttc        674
Gly Ile Val Asp Asn Val Val Ile Thr Tyr Glu Glu Ala Leu Met Phe
        125                 130                 135 ggc gtc gtg tcc gat acg ctc gtg atc cgt tcg tat tgc ccc aac aaa        722
Gly Val Val Ser Asp Thr Leu Val Ile Arg Ser Tyr Cys Pro Asn Lys
140                 145                 150                 155 ccc ggc ttc tgg gcc gac aaa ccg atc gag agg caa gcc tg atg gcc         769
Pro Gly Phe Trp Ala Asp Lys Pro Ile Glu Arg Gln Ala     Met Ala
                160                 165                         170 gat acc gat acg caa aag gcc gac gtc gtc gtc gtt gga tcg ggt gtc        817
Asp Thr Asp Thr Gln Lys Ala Asp Val Val Val Val Gly Ser Gly Val
                175                 180                 185 gcg ggc gcg atc gtc gcg cat cag ctc gcg atg gcg ggc aag gcg gtg        865
Ala Gly Ala Ile Val Ala His Gln Leu Ala Met Ala Gly Lys Ala Val
                190                 195                 200 atc ctg ctc gaa gcg ggc ccg cgc atg ccg cgc tgg gaa atc gtc gag        913
Ile Leu Leu Glu Ala Gly Pro Arg Met Pro Arg Trp Glu Ile Val Glu
            205                 210                 215 cgc ttc cgc aat cag ccc gac aag atg gac ttc atg gcg ccg tac ccg        961
Arg Phe Arg Asn Gln Pro Asp Lys Met Asp Phe Met Ala Pro Tyr Pro
    220                 225                 230 tcg agc ccc tgg gcg ccg cat ccc gag tac ggc ccg ccg aac gac tac       1009
Ser Ser Pro Trp Ala Pro His Pro Glu Tyr Gly Pro Pro Asn Asp Tyr
235                 240                 245                 250 ctg atc ctg aag ggc gag cac aag ttc aac tcg cag tac atc cgc gcg       1057
Leu Ile Leu Lys Gly Glu His Lys Phe Asn Ser Gln Tyr Ile Arg Ala
                255                 260                 265 gtg ggc ggc acg acg tgg cac tgg gcc gcg tcg gcg tgg cgc ttc att       1105
Val Gly Gly Thr Thr Trp His Trp Ala Ala Ser Ala Trp Arg Phe Ile
                270                 275                 280 ccg aac gac ttc aag atg aag agc gtg tac ggc gtc ggc cgc gac tgg       1153
Pro Asn Asp Phe Lys Met Lys Ser Val Tyr Gly Val Gly Arg Asp Trp
            285                 290                 295 ccg atc cag tac gac gat ctc gag ccg tac tat cag cgc gcg gag gaa       1201
Pro Ile Gln Tyr Asp Asp Leu Glu Pro Tyr Tyr Gln Arg Ala Glu Glu
        300                 305                 310 gag ctc ggc gtg tgg ggc ccg ggc ccc gag gaa gat ctg tac tcg ccg       1249
Glu Leu Gly Val Trp Gly Pro Gly Pro Glu Glu Asp Leu Tyr Ser Pro
315                 320                 325                 330 cgc aag cag ccg tat ccg atg ccg ccg ctg ccg ttg tcg ttc aac gag       1297
Arg Lys Gln Pro Tyr Pro Met Pro Pro Leu Pro Leu Ser Phe Asn Glu
                335                 340                 345 cag acc atc aag acg gcg ctg aac aac tac gat ccg aag ttc cat gtc       1345
Gln Thr Ile Lys Thr Ala Leu Asn Asn Tyr Asp Pro Lys Phe His Val
            350                 355                 360 gtg acc gag ccg gtc gcg cgc aac agc cgc ccg tac gac ggc cgc ccg       1393
Val Thr Glu Pro Val Ala Arg Asn Ser Arg Pro Tyr Asp Gly Arg Pro
        365                 370                 375 act tgt tgc ggc aac aac aac tgc atg ccg atc tgc ccg atc ggc gcg       1441
Thr Cys Cys Gly Asn Asn Asn Cys Met Pro Ile Cys Pro Ile Gly Ala
380                 385                 390 atg tac aac ggc atc gtg cac gtc gag aag gcc gaa cgc gcc ggc gcg       1489
Met Tyr Asn Gly Ile Val His Val Glu Lys Ala Glu Arg Ala Gly Ala
395                 400                 405                 410
```

-continued

| | | |
|---|---|---|
| aag ctg atc gag aac gcg gtc gtc tac aag ctc gag acg ggc ccg gac<br>Lys Leu Ile Glu Asn Ala Val Val Tyr Lys Leu Glu Thr Gly Pro Asp<br>415                      420                      425 | 1537 |
| aag cgc atc gtc gcg gcg ctc tac aag gac aag acg ggc gcc gag cat<br>Lys Arg Ile Val Ala Ala Leu Tyr Lys Asp Lys Thr Gly Ala Glu His<br>         430                      435                      440 | 1585 |
| cgc gtc gaa ggc aag tat ttc gtg ctc gcc gcg aac ggc atc gag acg<br>Arg Val Glu Gly Lys Tyr Phe Val Leu Ala Ala Asn Gly Ile Glu Thr<br>                445                      450                      455 | 1633 |
| ccg aag atc ctg ctg atg tcc gcg aac cgc gat ttc ccg aac ggt gtc<br>Pro Lys Ile Leu Leu Met Ser Ala Asn Arg Asp Phe Pro Asn Gly Val<br>460                      465                      470 | 1681 |
| gcg aac agc tcg gac atg gtc ggc cgc aac ctg atg gac cat ccg ggc<br>Ala Asn Ser Ser Asp Met Val Gly Arg Asn Leu Met Asp His Pro Gly<br>475                      480                      485                      490 | 1729 |
| acc ggc gtg tcg ttc tat gcg agc gag aag ctg tgg ccg ggc cgc ggc<br>Thr Gly Val Ser Phe Tyr Ala Ser Glu Lys Leu Trp Pro Gly Arg Gly<br>                495                      500                      505 | 1777 |
| ccg cag gag atg acg tcg ctg atc ggt ttc cgc gac ggt ccg ttc cgc<br>Pro Gln Glu Met Thr Ser Leu Ile Gly Phe Arg Asp Gly Pro Phe Arg<br>              510                      515                      520 | 1825 |
| gcg acc gaa gcg gcg aag aag atc cac ctg tcg aac ctg tcg cgc atc<br>Ala Thr Glu Ala Ala Lys Lys Ile His Leu Ser Asn Leu Ser Arg Ile<br>525                      530                      535 | 1873 |
| gac cag gag acg cag aag atc ttc aag gcc ggc aag ctg atg aag ccc<br>Asp Gln Glu Thr Gln Lys Ile Phe Lys Ala Gly Lys Leu Met Lys Pro<br>540                      545                      550 | 1921 |
| gac gag ctc gac gcg cag atc cgc gac cgt tcc gca cgc tac gtg cag<br>Asp Glu Leu Asp Ala Gln Ile Arg Asp Arg Ser Ala Arg Tyr Val Gln<br>555                      560                      565                      570 | 1969 |
| ttc gac tgc ttc cac gaa atc ctg ccg caa ccc gag aac cgc atc gtg<br>Phe Asp Cys Phe His Glu Ile Leu Pro Gln Pro Glu Asn Arg Ile Val<br>                575                      580                      585 | 2017 |
| ccg agc aag acg gcg acc gat gcg atc ggc att ccg cgc ccc gag atc<br>Pro Ser Lys Thr Ala Thr Asp Ala Ile Gly Ile Pro Arg Pro Glu Ile<br>              590                      595                      600 | 2065 |
| acg tat gcg atc gac gac tac gtg aag cgc ggc gcc gcg cat acg cgc<br>Thr Tyr Ala Ile Asp Asp Tyr Val Lys Arg Gly Ala Ala His Thr Arg<br>              605                      610                      615 | 2113 |
| gag gtc tac gcg acc gcc gcg aag gtg ctc ggc ggc acg gac gtc gtg<br>Glu Val Tyr Ala Thr Ala Ala Lys Val Leu Gly Gly Thr Asp Val Val<br>620                      625                      630 | 2161 |
| ttc aac gac gaa ttc gcg ccg aac aat cac atc acg ggc tcg acg atc<br>Phe Asn Asp Glu Phe Ala Pro Asn Asn His Ile Thr Gly Ser Thr Ile<br>635                      640                      645                      650 | 2209 |
| atg ggc gcc gat gcg cgc gac tcc gtc gtc gac aag gac tgc cgc acg<br>Met Gly Ala Asp Ala Arg Asp Ser Val Val Asp Lys Asp Cys Arg Thr<br>                655                      660                      665 | 2257 |
| ttc gac cat ccg aac ctg ttc att tcg agc agc gcg acg atg ccg acc<br>Phe Asp His Pro Asn Leu Phe Ile Ser Ser Ser Ala Thr Met Pro Thr<br>              670                      675                      680 | 2305 |
| gtc ggt acc gta aac gtg acg ctg acg atc gcc gcg ctc gcg ctg cgg<br>Val Gly Thr Val Asn Val Thr Leu Thr Ile Ala Ala Leu Ala Leu Arg<br>              685                      690                      695 | 2353 |
| atg tcg gac acg ctg aag aag gaa gtc tgacc gtg cgg aaa tct act ctc<br>Met Ser Asp Thr Leu Lys Lys Glu Val      Val Arg Lys Ser Thr Leu<br>700                      705                                          710 | 2403 |
| act ttc ctc atc gcc ggc tgc ctc gcg ttg ccg ggc ttc gcg cgc gcg<br>Thr Phe Leu Ile Ala Gly Cys Leu Ala Leu Pro Gly Phe Ala Arg Ala<br>715                      720                      725 | 2451 |

```
gcc gat gcg gcc gat ccg gcg ctg gtc aag cgc ggc gaa tac ctc gcg     2499
Ala Asp Ala Ala Asp Pro Ala Leu Val Lys Arg Gly Glu Tyr Leu Ala
730             735                 740                 745 acc gcc ggc gac tgc atg gcc tgc cac acc gtg aag ggc ggc aag ccg     2547
Thr Ala Gly Asp Cys Met Ala Cys His Thr Val Lys Gly Gly Lys Pro
                750                 755                 760 tac gcg ggc ggc ctt ggc atg ccg gta ccg atg ctc ggc aag atc tac     2595
Tyr Ala Gly Gly Leu Gly Met Pro Val Pro Met Leu Gly Lys Ile Tyr
            765                 770                 775 acg agc aac atc acg ccc gat ccc gat acg ggc atc ggc aaa tgg acg     2643
Thr Ser Asn Ile Thr Pro Asp Pro Asp Thr Gly Ile Gly Lys Trp Thr
        780                 785                 790 ttc gag gac ttc gag cgc gcg gtg cgg cac ggc gtg tcg aag aac ggc     2691
Phe Glu Asp Phe Glu Arg Ala Val Arg His Gly Val Ser Lys Asn Gly
    795                 800                 805 gac aac ctg tat ccg gcg atg ccg tac gtg tcg tac gcg aag atc acg     2739
Asp Asn Leu Tyr Pro Ala Met Pro Tyr Val Ser Tyr Ala Lys Ile Thr
810                 815                 820                 825 gac gac gac gta cgc gcg ctg tac gcc tac ttc atg cac ggc gtc gag     2787
Asp Asp Asp Val Arg Ala Leu Tyr Ala Tyr Phe Met His Gly Val Glu
                830                 835                 840 ccg gtc aag cag gcg ccg ccg aag aac gag att ccc gcg ctg ctc agc     2835
Pro Val Lys Gln Ala Pro Pro Lys Asn Glu Ile Pro Ala Leu Leu Ser
            845                 850                 855 atg cgc tgg ccg ctg aag atc tgg aac tgg ctg ttc ctg aag gac ggc     2883
Met Arg Trp Pro Leu Lys Ile Trp Asn Trp Leu Phe Leu Lys Asp Gly
        860                 865                 870 ccg tac cag ccg aag ccg tcg cag agc gcc gaa tgg aat cgc ggc gcg     2931
Pro Tyr Gln Pro Lys Pro Ser Gln Ser Ala Glu Trp Asn Arg Gly Ala
    875                 880                 885 tat ctg gtg cag ggt ctc gcg cac tgc agc acg tgc cac acg ccg cgc     2979
Tyr Leu Val Gln Gly Leu Ala His Cys Ser Thr Cys His Thr Pro Arg
890                 895                 900                 905 ggc atc gcg atg cag gag aag tcg ctc gac gaa acc ggc ggc agc ttc     3027
Gly Ile Ala Met Gln Glu Lys Ser Leu Asp Glu Thr Gly Gly Ser Phe
                910                 915                 920 ctc gcg ggg tcg gtg ctc gcc ggc tgg gac ggc tac aac atc acg tcg     3075
Leu Ala Gly Ser Val Leu Ala Gly Trp Asp Gly Tyr Asn Ile Thr Ser
            925                 930                 935 gac ccg aat gcg ggg atc ggc agc tgg acg cag cag cag ctc gtg cag     3123
Asp Pro Asn Ala Gly Ile Gly Ser Trp Thr Gln Gln Gln Leu Val Gln
        940                 945                 950 tat ttg cgc acc ggc agc gtg ccg ggc gtc gcg cag gcg gcc ggg ccg     3171
Tyr Leu Arg Thr Gly Ser Val Pro Gly Val Ala Gln Ala Ala Gly Pro
    955                 960                 965 atg gcc gag gcg gtc gag cac agc ttc tcg aag atg acc gaa gcg gac     3219
Met Ala Glu Ala Val Glu His Ser Phe Ser Lys Met Thr Glu Ala Asp
970                 975                 980                 985 atc ggt gcg atc gcc acg tac gtc cgc acg gtg ccg gcc gtt gcc gac     3267
Ile Gly Ala Ile Ala Thr Tyr Val Arg Thr Val Pro Ala Val Ala Asp
                990                 995                 1000 agc aac gcg aag cag ccg cgg tcg tcg tgg ggc aag ccg gcc     gag     3312
Ser Asn Ala Lys Gln Pro Arg Ser Ser Trp Gly Lys Pro Ala         Glu
            1005                1010                1015 gac ggg ctg aag ctg cgc ggt gtc gcg ctc gcg tcg tcg ggc     atc     3357
Asp Gly Leu Lys Leu Arg Gly Val Ala Leu Ala Ser Ser Gly         Ile
        1020                1025                1030 gat ccg gcg cgg ctg tat ctc ggc aac tgc gcg acg tgc cac cag         3402
Asp Pro Ala Arg Leu Tyr Leu Gly Asn Cys Ala Thr Cys His Gln
```

```
                    1035                1040                1045
atg cag ggc aag ggc acg ccg gac ggc tat tac ccg tcg ctg ttc       3447
Met Gln Gly Lys Gly Thr Pro Asp Gly Tyr Tyr Pro Ser Leu Phe
            1050                1055                1060 cac aac tcc acc gtc ggc gcg tcg aat ccg tcg aac ctc gtg cag       3492
His Asn Ser Thr Val Gly Ala Ser Asn Pro Ser Asn Leu Val Gln
            1065                1070                1075 gtg atc ctg aac ggc gtg cag cgc aag atc ggc agc gag gat atc       3537
Val Ile Leu Asn Gly Val Gln Arg Lys Ile Gly Ser Glu Asp Ile
            1080                1085                1090 ggg atg ccc gct ttc cgc tac gat ctg aac gac gcg cag atc gcc       3582
Gly Met Pro Ala Phe Arg Tyr Asp Leu Asn Asp Ala Gln Ile Ala
            1095                1100                1105 gcg ctg acg aac tac gtg acc gcg cag ttc ggc aat ccg gcg gcg       3627
Ala Leu Thr Asn Tyr Val Thr Ala Gln Phe Gly Asn Pro Ala Ala
            1110                1115                1120 aag gtg acg gag cag gac gtc gcg aag ctg cgc tgacatagtc            3670
Lys Val Thr Glu Gln Asp Val Ala Lys Leu Arg
            1125                1130 gggcgcgccg acacggcgca accgatagga caggag                           3706

<210> SEQ ID NO 2
<211> LENGTH: 168
<212> TYPE: PRT
<213> ORGANISM: Burkholderia cepacia

<400> SEQUENCE: 2

Met His Asn Asp Asn Thr Pro His Ser Arg Arg His Gly Asp Ala Ala
1               5                   10                  15

Ala Ser Gly Ile Thr Arg Arg Gln Trp Leu Gln Gly Ala Leu Ala Leu
            20                  25                  30

Thr Ala Ala Gly Leu Thr Gly Ser Leu Thr Leu Arg Ala Leu Ala Asp
        35                  40                  45

Asn Pro Gly Thr Ala Pro Leu Asp Thr Phe Met Thr Leu Ser Glu Ser
    50                  55                  60

Leu Thr Gly Lys Lys Gly Leu Ser Arg Val Ile Gly Glu Arg Leu Leu
65                  70                  75                  80

Gln Ala Leu Gln Lys Gly Ser Phe Lys Thr Ala Asp Ser Leu Pro Gln
                85                  90                  95

Leu Ala Gly Ala Leu Ala Ser Gly Ser Leu Thr Pro Glu Gln Glu Ser
            100                 105                 110

Leu Ala Leu Thr Ile Leu Glu Ala Trp Tyr Leu Gly Ile Val Asp Asn
        115                 120                 125

Val Val Ile Thr Tyr Glu Glu Ala Leu Met Phe Gly Val Val Ser Asp
    130                 135                 140

Thr Leu Val Ile Arg Ser Tyr Cys Pro Asn Lys Pro Gly Phe Trp Ala
145                 150                 155                 160

Asp Lys Pro Ile Glu Arg Gln Ala
                165

<210> SEQ ID NO 3
<211> LENGTH: 539
<212> TYPE: PRT
<213> ORGANISM: Burkholderia cepacia

<400> SEQUENCE: 3

Met Ala Asp Thr Asp Thr Gln Lys Ala Asp Val Val Val Val Gly Ser
1               5                   10                  15
```

```
Gly Val Ala Gly Ala Ile Val Ala His Gln Leu Ala Met Ala Gly Lys
            20                  25                  30
Ala Val Ile Leu Leu Glu Ala Gly Pro Arg Met Pro Arg Trp Glu Ile
        35                  40                  45
Val Glu Arg Phe Arg Asn Gln Pro Asp Lys Met Asp Phe Met Ala Pro
 50                  55                  60
Tyr Pro Ser Ser Pro Trp Ala Pro His Pro Glu Tyr Gly Pro Pro Asn
 65                  70                  75                  80
Asp Tyr Leu Ile Leu Lys Gly Glu His Lys Phe Asn Ser Gln Tyr Ile
                85                  90                  95
Arg Ala Val Gly Gly Thr Thr Trp His Trp Ala Ala Ser Ala Trp Arg
                100                 105                 110
Phe Ile Pro Asn Asp Phe Lys Met Lys Ser Val Tyr Gly Val Gly Arg
            115                 120                 125
Asp Trp Pro Ile Gln Tyr Asp Asp Leu Glu Pro Tyr Tyr Gln Arg Ala
        130                 135                 140
Glu Glu Glu Leu Gly Val Trp Gly Pro Gly Pro Glu Glu Asp Leu Tyr
145                 150                 155                 160
Ser Pro Arg Lys Gln Pro Tyr Pro Met Pro Pro Leu Pro Leu Ser Phe
                165                 170                 175
Asn Glu Gln Thr Ile Lys Thr Ala Leu Asn Asn Tyr Asp Pro Lys Phe
                180                 185                 190
His Val Val Thr Glu Pro Val Ala Arg Asn Ser Arg Pro Tyr Asp Gly
            195                 200                 205
Arg Pro Thr Cys Cys Gly Asn Asn Cys Met Pro Ile Cys Pro Ile
        210                 215                 220
Gly Ala Met Tyr Asn Gly Ile Val His Val Glu Lys Ala Glu Arg Ala
225                 230                 235                 240
Gly Ala Lys Leu Ile Glu Asn Ala Val Val Tyr Lys Leu Glu Thr Gly
                245                 250                 255
Pro Asp Lys Arg Ile Val Ala Ala Leu Tyr Lys Asp Lys Thr Gly Ala
                260                 265                 270
Glu His Arg Val Glu Gly Lys Tyr Phe Val Leu Ala Ala Asn Gly Ile
            275                 280                 285
Glu Thr Pro Lys Ile Leu Leu Met Ser Ala Asn Arg Asp Phe Pro Asn
        290                 295                 300
Gly Val Ala Asn Ser Ser Asp Met Val Gly Arg Asn Leu Met Asp His
305                 310                 315                 320
Pro Gly Thr Gly Val Ser Phe Tyr Ala Ser Glu Lys Leu Trp Pro Gly
                325                 330                 335
Arg Gly Pro Gln Glu Met Thr Ser Leu Ile Gly Phe Arg Asp Gly Pro
                340                 345                 350
Phe Arg Ala Thr Glu Ala Ala Lys Lys Ile His Leu Ser Asn Leu Ser
            355                 360                 365
Arg Ile Asp Gln Glu Thr Gln Lys Ile Phe Lys Ala Gly Lys Leu Met
        370                 375                 380
Lys Pro Asp Glu Leu Asp Ala Gln Ile Arg Asp Arg Ser Ala Arg Tyr
385                 390                 395                 400
Val Gln Phe Asp Cys Phe His Glu Ile Leu Pro Gln Pro Glu Asn Arg
                405                 410                 415
Ile Val Pro Ser Lys Thr Ala Asp Ala Ile Gly Ile Pro Arg Pro
            420                 425                 430
```

```
Glu Ile Thr Tyr Ala Ile Asp Asp Tyr Val Lys Arg Gly Ala Ala His
            435                 440                 445

Thr Arg Glu Val Tyr Ala Thr Ala Lys Val Leu Gly Gly Thr Asp
450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
                500                 505                 510

Pro Thr Val Gly Thr Val Asn Val Thr Leu Thr Ile Ala Ala Leu Ala
                515                 520                 525

Leu Arg Met Ser Asp Thr Leu Lys Lys Glu Val
530                 535

<210> SEQ ID NO 4
<211> LENGTH: 425
<212> TYPE: PRT
<213> ORGANISM: Burkholderia cepacia

<400> SEQUENCE: 4

Met Arg Lys Ser Thr Leu Thr Phe Leu Ile Ala Gly Cys Leu Ala Leu
1               5                   10                  15

Pro Gly Phe Ala Arg Ala Ala Asp Ala Ala Asp Pro Ala Leu Val Lys
                20                  25                  30

Arg Gly Glu Tyr Leu Ala Thr Ala Gly Asp Cys Met Ala Cys His Thr
            35                  40                  45

Val Lys Gly Gly Lys Pro Tyr Ala Gly Leu Gly Met Pro Val Pro
50                  55                  60

Met Leu Gly Lys Ile Tyr Thr Ser Asn Ile Thr Pro Asp Pro Asp Thr
65                  70                  75                  80

Gly Ile Gly Lys Trp Thr Phe Glu Asp Phe Glu Arg Ala Val Arg His
                85                  90                  95

Gly Val Ser Lys Asn Gly Asp Asn Leu Tyr Pro Ala Met Pro Tyr Val
                100                 105                 110

Ser Tyr Ala Lys Ile Thr Asp Asp Val Arg Ala Leu Tyr Ala Tyr
            115                 120                 125

Phe Met His Gly Val Glu Pro Val Lys Gln Ala Pro Pro Lys Asn Glu
130                 135                 140

Ile Pro Ala Leu Leu Ser Met Arg Trp Pro Leu Lys Ile Trp Asn Trp
145                 150                 155                 160

Leu Phe Leu Lys Asp Gly Pro Tyr Gln Pro Lys Pro Ser Gln Ser Ala
                165                 170                 175

Glu Trp Asn Arg Gly Ala Tyr Leu Val Gln Gly Leu Ala His Cys Ser
                180                 185                 190

Thr Cys His Thr Pro Arg Gly Ile Ala Met Gln Glu Lys Ser Leu Asp
            195                 200                 205

Glu Thr Gly Gly Ser Phe Leu Ala Gly Ser Val Leu Ala Gly Trp Asp
210                 215                 220

Gly Tyr Asn Ile Thr Ser Asp Pro Asn Ala Gly Ile Gly Ser Trp Thr
225                 230                 235                 240

Gln Gln Gln Leu Val Gln Tyr Leu Arg Thr Gly Ser Val Pro Gly Val
                245                 250                 255

Ala Gln Ala Ala Gly Pro Met Ala Glu Ala Val Glu His Ser Phe Ser
                260                 265                 270
```

Lys Met Thr Glu Ala Asp Ile Gly Ala Ile Ala Thr Tyr Val Arg Thr
      275                 280                 285

Val Pro Ala Val Ala Asp Ser Asn Ala Lys Gln Pro Arg Ser Ser Trp
      290                 295                 300

Gly Lys Pro Ala Glu Asp Gly Leu Lys Leu Arg Gly Val Ala Leu Ala
305                 310                 315                 320

Ser Ser Gly Ile Asp Pro Ala Arg Leu Tyr Leu Gly Asn Cys Ala Thr
                325                 330                 335

Cys His Gln Met Gln Gly Lys Gly Thr Pro Asp Gly Tyr Tyr Pro Ser
            340                 345                 350

Leu Phe His Asn Ser Thr Val Gly Ala Ser Asn Pro Ser Asn Leu Val
        355                 360                 365

Gln Val Ile Leu Asn Gly Val Gln Arg Lys Ile Gly Ser Glu Asp Ile
    370                 375                 380

Gly Met Pro Ala Phe Arg Tyr Asp Leu Asn Asp Ala Gln Ile Ala Ala
385                 390                 395                 400

Leu Thr Asn Tyr Val Thr Ala Gln Phe Gly Asn Pro Ala Ala Lys Val
                405                 410                 415

Thr Glu Gln Asp Val Ala Lys Leu Arg
            420                 425

<210> SEQ ID NO 5
<211> LENGTH: 5
<212> TYPE: PRT
<213> ORGANISM: Artificial Sequence
<220> FEATURE:
<223> OTHER INFORMATION: heme binding site
<220> FEATURE:
<221> NAME/KEY: misc_feature
<222> LOCATION: (2)..(3)
<223> OTHER INFORMATION: Xaa can be any naturally occurring amino acid

<400> SEQUENCE: 5

Cys Xaa Xaa Cys His
1               5

<210> SEQ ID NO 6
<211> LENGTH: 425
<212> TYPE: PRT
<213> ORGANISM: Burkholderia cepacia

<400> SEQUENCE: 6

Met Arg Lys Ser Thr Leu Thr Phe Leu Leu Ala Gly Cys Leu Ala Leu
1               5                   10                  15

Pro Gly Leu Ala Arg Ala Ala Asp Ser Ala Asp Pro Ala Gln Val Lys
            20                  25                  30

Arg Gly Glu Tyr Leu Ala Val Ala Gly Asp Cys Met Ala Cys His Thr
        35                  40                  45

Ala Lys Gly Gly Lys Pro Phe Ala Gly Leu Gly Met Pro Val Pro
    50                  55                  60

Met Leu Gly Lys Ile Tyr Thr Ser Asn Ile Thr Pro Asp Pro Asp Thr
65                  70                  75                  80

Gly Ile Gly Asn Trp Thr Phe Glu Asp Phe Glu Arg Ala Val Arg His
                85                  90                  95

Gly Val Ser Lys Asn Gly Asp Asn Leu Tyr Pro Ala Met Pro Tyr Val
            100                 105                 110

Ser Tyr Ala Lys Ile Asn Asp Asp Asp Val Gln Ala Leu Tyr Ala Tyr
        115                 120                 125

-continued

```
Phe Met His Gly Val Glu Pro Val Lys Gln Ala Pro Pro Lys Asn Glu
    130                 135                 140

Ile Pro Ala Leu Leu Ser Met Arg Trp Pro Leu Lys Ile Trp Asn Trp
145                 150                 155                 160
Leu Phe Leu Lys Asp Gly Val Tyr Gln Pro Lys Pro Glu Gln Ser Ala
                165                 170                 175
Glu Trp Asn Arg Gly Ala Tyr Leu Val Gln Gly Leu Ala His Cys Ser
            180                 185                 190
Thr Cys His Thr Pro Arg Gly Ile Ala Met Gln Glu Lys Ser Leu Asp
        195                 200                 205
Glu Thr Gly Gly Ser Phe Leu Ser Gly Ser Val Leu Ala Gly Trp Asp
    210                 215                 220
Gly Tyr Asn Ile Thr Ser Asp Pro Asn Ala Gly Ile Gly Gly Trp Thr
225                 230                 235                 240
Gln Gln Gln Leu Val Gln Tyr Leu Arg Thr Gly Ser Val Pro Gly Leu
                245                 250                 255
Ala Gln Ala Ala Gly Pro Met Ala Glu Ala Ile Glu His Ser Phe Ser
            260                 265                 270
Lys Met Thr Glu Ala Asp Ile Gly Ala Ile Ser Thr Tyr Ile Arg Thr
        275                 280                 285
Val Pro Ala Val Ala Ser Gly Asp Ala Lys Gln Ser Arg Ser Ser Trp
    290                 295                 300
Gly Lys Pro Ala Glu Asp Gly Leu Lys Leu Arg Gly Val Ala Leu Ala
305                 310                 315                 320
Ser Ser Gly Ile Asp Pro Ala Arg Leu Tyr Leu Gly Asn Cys Ala Thr
                325                 330                 335
Cys His Gln Met Gln Gly Lys Gly Thr Pro Asp Gly Tyr Tyr Pro Pro
            340                 345                 350
Leu Phe His Asn Ser Thr Val Gly Ala Ser Asn Pro Thr Asn Leu Val
        355                 360                 365
Gln Val Ile Leu Asn Gly Val Gln Arg Lys Ala Gly Ser Glu Asp Val
    370                 375                 380
Gly Met Pro Ala Phe Arg His Glu Leu Ser Asp Ala Gln Ile Ala Ala
385                 390                 395                 400
Leu Thr Asn Tyr Leu Thr Gly Gln Phe Gly Asn Pro Ala Ala Lys Val
                405                 410                 415
Thr Glu Gln Asp Val Ala Lys Leu Arg
            420                 425

<210> SEQ ID NO 7
<211> LENGTH: 428
<212> TYPE: PRT
<213> ORGANISM: Burkholderia cenocepacia

<400> SEQUENCE: 7

Met Arg Leu Pro Gly Leu Ser Val Leu Val Val Phe Phe Leu Ile Ala
1               5                   10                  15

Thr Asp Pro Ala Ser Ala Ala Gly Gln Ala Ala Asp Arg Ile Ala Ala
            20                  25                  30

Gly Lys Ala Leu Ala Val Ala Ala Asp Cys Val Ala Cys His Thr Val
        35                  40                  45

Gln Gly Gly Gln Pro Phe Ala Gly Gly Leu Ala Met Pro Leu Pro Met
    50                  55                  60

Gly Asp Ile Tyr Ser Thr Asn Ile Thr Pro Asp Arg Gln Thr Gly Ile
```

```
            65                  70                  75                  80
Gly Asn Tyr Ser Glu Arg Asp Phe Ala Asn Val Leu Arg Lys Gly Leu
                    85                  90                  95

Arg Arg Asp Gly Gly Asn Leu Tyr Pro Ala Met Pro Tyr Pro Ser Tyr
            100                 105                 110

Thr Lys Phe Ser Asp Asp Asp Ile Ala Asn Leu Tyr Ala Tyr Phe Met
            115                 120                 125

Gln Gly Val Ala Pro Val Arg Gln Pro Asn Arg Ala Pro Asp Phe Pro
130                 135                 140

Trp Pro Leu Thr Met Arg Trp Pro Leu Lys Ile Trp Asn Ala Leu Tyr
145                 150                 155                 160

Leu Arg Glu Gly Ala Tyr Val Pro Lys Pro Gly Arg Asp Ala Glu Trp
                    165                 170                 175

Asn Arg Gly Ala Tyr Leu Val Gln Gly Ala His Cys Gly Thr Cys
            180                 185                 190

His Thr Pro Arg Gly Ile Gly Met Gln Glu Leu Ala Tyr Asp Glu Thr
            195                 200                 205

Gly Val Gly Tyr Leu Ala Gly Ala Pro Leu Ala Gly Trp Gln Ala Phe
            210                 215                 220

Asn Ile Thr His Asp Arg Asp Ala Gly Ile Gly Thr Trp Thr Ala
225                 230                 235                 240

Gln Ile Val Gln Tyr Leu Arg Thr Gly Asn Val Pro Gly Lys Ala Gln
                    245                 250                 255

Ala Ala Gly Pro Met Ala Glu Ala Val Glu His Ser Phe Ser Arg Met
            260                 265                 270

Ser Glu Arg Asp Leu Asn Ala Ile Ala Val Tyr Leu Ser Thr Val Pro
            275                 280                 285

Ala Ala Lys Gly Ala Asp Thr Ala Pro Arg Ser Thr Gln Gly Arg Pro
            290                 295                 300

Thr Asp Asp Tyr Val Ala Ile Arg Ala Ala Ala Ala Gly Ser Trp
305                 310                 315                 320

Thr Pro Ala Gly Ala Ser Leu Tyr Leu Asp His Cys Ala Ser Cys His
                    325                 330                 335

Gly Met Thr Gly Ala Gly Thr Thr Asp Gly Phe Pro Ser Leu Phe
            340                 345                 350

Ala Asn Ser Ala Val Gly Thr Ala Thr Ala Ser Asn Leu Leu Gln Val
            355                 360                 365

Val Met His Gly Ala Ser Val Asn Asn Gly Thr Thr His Tyr Phe Met
370                 375                 380

Pro Ala Phe Gln Thr Glu Leu Asp Asp Asp Glu Val Val Thr Leu Val
385                 390                 395                 400

Asn Tyr Leu Ser Glu Arg Phe Gly Asn Gly Arg Ala Arg Val Ser Ala
                    405                 410                 415

Ala Glu Val Ala Lys Ile Arg Thr Ala Pro Ala His
            420                 425

<210> SEQ ID NO 8
<211> LENGTH: 425
<212> TYPE: PRT
<213> ORGANISM: Burkholderia multivorans

<400> SEQUENCE: 8

Met Arg Lys Ser Thr Leu Thr Phe Leu Ile Ala Gly Cys Leu Ala Leu
1               5                   10                  15
```

```
Pro Gly Leu Ala Arg Ala Ala Asp Ala Ala Asp Pro Ala Leu Val Lys
            20                  25                  30

Arg Gly Glu Tyr Leu Ala Thr Ala Gly Asp Cys Met Ala Cys His Thr
        35                  40                  45

Val Lys Gly Gly Lys Pro Tyr Ala Gly Leu Gly Met Pro Val Pro
50                  55                  60

Met Leu Gly Lys Ile Tyr Thr Ser Asn Ile Thr Pro Asp Pro Asp Thr
65                  70                  75                  80

Gly Ile Gly Lys Trp Thr Phe Glu Asp Phe Glu Arg Ala Val Arg His
                85                  90                  95

Gly Val Ser Lys Asn Gly Asp Asn Leu Tyr Pro Ala Met Pro Tyr Val
            100                 105                 110

Ser Tyr Ala Lys Ile Thr Asp Asp Val Arg Ala Leu Tyr Ala Tyr
        115                 120                 125

Phe Met His Gly Val Glu Pro Val Lys Gln Ala Pro Pro Lys Asn Glu
    130                 135                 140

Ile Pro Ala Leu Leu Ser Met Arg Trp Pro Leu Lys Ile Trp Asn Trp
145                 150                 155                 160

Leu Phe Leu Lys Asp Gly Pro Tyr Gln Pro Lys Pro Ser Gln Ser Ala
                165                 170                 175

Glu Trp Asn Arg Gly Ala Tyr Leu Val Gln Gly Leu Ala His Cys Ser
            180                 185                 190

Thr Cys His Thr Pro Arg Gly Ile Ala Met Gln Glu Lys Ser Leu Asp
        195                 200                 205

Glu Thr Gly Gly Ser Phe Leu Ala Gly Ser Val Leu Ala Gly Trp Asp
    210                 215                 220

Gly Tyr Asn Ile Thr Ser Asp Pro Asn Ala Gly Ile Gly Ser Trp Thr
225                 230                 235                 240

Gln Gln Gln Leu Val Gln Tyr Leu Arg Thr Gly Ser Val Pro Gly Val
                245                 250                 255

Ala Gln Ala Ala Gly Pro Met Ala Glu Ala Val Glu His Ser Phe Ser
            260                 265                 270

Lys Met Thr Glu Ala Asp Ile Gly Ala Ile Ala Thr Tyr Val Arg Thr
        275                 280                 285

Val Pro Ala Val Ala Asp Ser Asn Ala Lys Gln Pro Arg Ser Ser Trp
    290                 295                 300

Gly Lys Pro Ala Glu Asp Gly Leu Lys Leu Arg Gly Val Ala Leu Ala
305                 310                 315                 320

Ser Ser Gly Ile Asp Pro Ala Arg Leu Tyr Leu Gly Asn Cys Ala Thr
                325                 330                 335

Cys His Gln Met Gln Gly Lys Gly Thr Pro Asp Gly Tyr Tyr Pro Ser
            340                 345                 350

Leu Phe His Asn Ser Thr Val Gly Ala Ser Asn Pro Ser Asn Leu Val
        355                 360                 365

Gln Val Ile Leu Asn Gly Val Gln Arg Lys Ile Gly Ser Glu Asp Ile
    370                 375                 380

Gly Met Pro Ala Phe Arg Tyr Asp Leu Asn Asp Ala Gln Ile Ala Ala
385                 390                 395                 400

Leu Thr Asn Tyr Leu Thr Ala Gln Phe Gly Asn Pro Ala Ala Lys Val
                405                 410                 415

Thr Glu Gln Asp Val Ala Lys Leu Arg
        420                 425
```

```
<210> SEQ ID NO 9
<211> LENGTH: 425
<212> TYPE: PRT
<213> ORGANISM: Burkholderia ubonensis

<400> SEQUENCE

-continued

Gly Met Pro Ala Phe Arg His Glu Leu Ser Asp Ala Gln Ile Ala Ala
385                 390                 395                 400

Leu Ala Asn Tyr Leu Thr Gly Gln Phe Gly Asn Pro Ala Ala Lys Val
            405                 410                 415

Thr Glu Gln Asp Val Ala Lys Ala Arg
            420                 425

<210> SEQ ID NO 10
<211> LENGTH: 425
<212> TYPE: PRT
<213> ORGANISM: Burkholderia stagnalis

<400> SEQUENCE: 10

Met Leu Lys Gln Ser Leu Thr Phe Leu Leu Ala Gly Cys Leu Ala Leu
1               5                   10                  15

Pro Gly Leu Ala Arg Ala Ala Asp Pro Ala Asp Ala Ala Leu Val Lys
            20                  25                  30

Arg Gly Glu Tyr Leu Ala Val Ala Gly Asp Cys Met Ala Cys His Thr
        35                  40                  45

Val Lys Gly Gly Lys Pro Phe Ala Gly Leu Gly Met Pro Val Pro
50                  55                  60

Met Leu Gly Lys Ile Tyr Thr Ser Asn Ile Thr Pro Asp Ala Asp Thr
65                  70                  75                  80

Gly Ile Gly Gly Trp Thr Tyr Asp Asp Phe Glu Arg Ala Val Arg His
                85                  90                  95

Gly Val Ser Lys Asn Gly Asp Asn Leu Tyr Pro Ala Met Pro Tyr Val
            100                 105                 110

Ser Tyr Ala Lys Val Ser Asp Asp Val Lys Ala Leu Tyr Ala Tyr
        115                 120                 125

Phe Met His Gly Val Glu Pro Val Lys Gln Thr Pro Pro Lys Asn Glu
130                 135                 140

Ile Pro Ala Leu Leu Ser Met Arg Trp Pro Leu Lys Ile Trp Asn Trp
145                 150                 155                 160

Leu Phe Leu Lys Asp Gly Ala Tyr Gln Pro Lys Pro Ala Gln Ser Ala
                165                 170                 175

Glu Trp Asn Arg Gly Ala Tyr Leu Val Gln Gly Leu Ala His Cys Ser
            180                 185                 190

Thr Cys His Thr Pro Arg Gly Ile Ala Met Gln Glu Lys Ser Leu Asp
        195                 200                 205

Glu Thr Gly Gly Ser Phe Leu Ser Gly Ser Val Leu Ala Gly Trp Asp
210                 215                 220

Gly Tyr Asn Ile Thr Ser Asp Ala Asn Ala Gly Ile Gly Gly Trp Ser
225                 230                 235                 240

Gln Gln Gln Leu Val Gln Tyr Leu Arg Thr Gly Ser Val Pro Gly Val
                245                 250                 255

Ala Gln Ala Ala Gly Pro Met Ala Glu Ala Val Glu His Ser Phe Ser
            260                 265                 270

Lys Met Thr Asp Ala Asp Ile Gly Ala Ile Ala Thr Tyr Ile Arg Thr
        275                 280                 285

Val Pro Ala Val Ala Asp Ser Ser Val Lys Gln Pro Arg Ala Thr Trp
290                 295                 300

Gly Lys Pro Ala Glu Asp Gly Leu Arg Leu Arg Gly Val Ala Leu Ala
305                 310                 315                 320

Ser Ser Gly Ile Asp Pro Ala Arg Leu Tyr Leu Gly Asn Cys Ala Ser
                325                 330                 335

```
Cys His Gln Met Gln Gly Lys Gly Thr Pro Asp Gly Tyr Tyr Pro Ser
            340                 345                 350

Leu Phe His Asn Ser Thr Val Gly Ala Pro Asn Pro Thr Asn Leu Val
            355                 360                 365

Gln Val Ile Leu Asn Gly Val Gln Arg Lys Ala Gly Ser Glu Asp Val
        370                 375                 380

Gly Met Pro Ala Phe Arg His Glu Leu Ser Asp Ala Gln Ile Ala Ala
385                 390                 395                 400

Leu Ala Asn Tyr Leu Thr Gly Gln Phe Gly Asn Pro Ala Ala Lys Val
                405                 410                 415

Thr Glu Gln Asp Val Ala Lys Leu Arg
            420                 425

<210> SEQ ID NO 11
<211> LENGTH: 447
<212> TYPE: PRT
<213> ORGANISM: Burkholderia thailandensis

<400> SEQUENCE: 11

Met Leu Lys Arg Thr Leu Ser Phe Val Leu Ala Gly Cys Leu Ala Leu
1               5                   10                  15

Pro Gly Leu Ser Val Ala Ala Ser Ser Ala Pro Val Ala Ala Ala Thr
            20                  25                  30

Ser Ala Ala Ala Thr Ser Ala Ser Ala Pro Ser Ala Asp Ala
        35                  40                  45

Ala Leu Val Glu Arg Gly Arg Tyr Leu Ala Val Ala Gly Asp Cys Met
    50                  55                  60

Ala Cys His Thr Ala Lys Gly Gly Lys Pro Phe Ala Gly Gly Leu Pro
65                  70                  75                  80

Met Arg Ala Pro Leu Leu Gly Thr Ile Tyr Thr Thr Asn Ile Thr Pro
                85                  90                  95

Asp Lys Glu Thr Gly Ile Gly Asp Trp Thr Phe Ala Asp Phe Glu Arg
            100                 105                 110

Ala Val Arg His Gly Val Ala Lys Asn Gly Asp Asn Leu Tyr Pro Ala
        115                 120                 125

Met Pro Tyr Val Ser Tyr Ala Lys Val Thr Asp Asp Val Lys Ala
    130                 135                 140

Leu Tyr Ala Tyr Phe Thr His Gly Val Glu Pro Val Arg Gln Pro Pro
145                 150                 155                 160

Arg Lys Asn Asp Ile Pro Trp Tyr Leu Ser Met Arg Trp Pro Leu Lys
                165                 170                 175

Ile Trp Asn Leu Leu Phe Leu Lys Glu Gly Val Tyr Gln Pro Lys Pro
            180                 185                 190

Glu Arg Ser Val Glu Trp Asn Arg Gly Ala Tyr Leu Val Gln Gly Leu
        195                 200                 205

Ala His Cys Gly Thr Cys His Thr Pro Arg Ala Val Thr Leu Gln Glu
    210                 215                 220

Lys Ser Leu Asp Glu Thr Gly Gly Ser Phe Leu Ala Gly Ser Val Leu
225                 230                 235                 240

Ser Gly Trp Asp Gly Tyr Asn Ile Thr Ser Asp Thr Asn Ala Gly Ile
                245                 250                 255

Gly Gly Trp Ser Gln Gln Gln Leu Val Gln Tyr Leu Arg Thr Gly Ser
            260                 265                 270

Val Pro Gly Leu Ala Gln Ala Ala Gly Pro Met Ala Glu Ala Val Glu
```

-continued

```
        275                 280                 285

His Ser Phe Ser Gln Met Thr Asp Ala Asp Ile Gly Ala Ile Ala Thr
    290                 295                 300

Tyr Ile Arg Thr Val Pro Ala Val Ala Asp Gly Thr Ala Lys Ala Arg
305                 310                 315                 320

Ser Ala Trp Gly Lys Pro Ala Glu Asp Gly Ile Arg Leu Arg Gly Val
                325                 330                 335

Ala Leu Ala Ala Thr Gly Ile Asp Pro Ala Arg Leu Tyr Leu Gly Asn
            340                 345                 350

Cys Ala Ser Cys His Gln Met Gln Gly Lys Gly Thr Pro Asp Gly Tyr
        355                 360                 365

Tyr Pro Pro Leu Leu His Asn Ser Thr Val Gly Ala Pro Asn Pro Thr
    370                 375                 380

Asn Leu Val Gln Val Ile Leu Asn Gly Val Ala Arg Lys Ala Gly Gly
385                 390                 395                 400

Glu Asp Val Gly Met Pro Ala Phe Arg Arg Glu Leu Ser Asp Ala Gln
                405                 410                 415

Ile Ala Ala Leu Ala Asn Tyr Leu Thr Ala Gln Phe Gly Asn Pro Ala
            420                 425                 430

Ala Lys Val Ser Glu Gln Asp Val Ala Lys Leu Arg Ala Ala Gln
        435                 440                 445

<210> SEQ ID NO 12
<211> LENGTH: 431
<212> TYPE: PRT
<213> ORGANISM: Ralstonia solanacearum

<400> SEQUENCE: 12

Met Ser Lys Ala Thr Ala Gln Ala Ala Ser Phe Leu Leu Leu Ser Leu
1               5                   10                  15

Leu Gly Ala Ala Ala Val Ala Arg Gly Ala Asp Pro Pro Ala Asp Thr
            20                  25                  30

Ala Gln Ile Arg Arg Gly Glu Tyr Leu Ala Ile Ala Ala Asp Cys Val
        35                  40                  45

Ala Cys His Thr Ala Pro Gly Gly Lys Pro Phe Ala Gly Gly Leu Pro
    50                  55                  60

Leu Gln Ile Pro Met Leu Gly Thr Ile Tyr Ser Ser Asn Ile Thr Pro
65                  70                  75                  80

Asp Pro Asn Thr Gly Ile Gly Lys Trp Arg Tyr Glu Asp Phe Glu Arg
                85                  90                  95

Ala Val Arg Gln Gly Val Ser Asp Asp Gly Glu Asn Leu Tyr Pro Ala
            100                 105                 110

Met Pro Tyr Pro Ser Tyr Ala Lys Ile Asn Asp Ala Asp Met Arg Asp
        115                 120                 125

Leu Tyr Ala Tyr Phe Arg Tyr Gly Val Ala Ala Val Glu Ser Asp Pro
    130                 135                 140

Pro Pro Ser Thr Ile Arg Trp Pro Leu Asn Met Arg Trp Pro Leu Lys
145                 150                 155                 160

Leu Trp Asn Leu Ala Phe Leu Lys Ser Gly Pro Tyr Ile Pro Lys Gly
                165                 170                 175

Val Lys Thr Pro Thr Trp Asn Arg Gly Ala Tyr Leu Val Gln Gly Leu
            180                 185                 190

Ala His Cys Gly Thr Cys His Thr Pro Arg Gly Phe Ala Met Gln Glu
        195                 200                 205
```

```
Lys Ala Met Asp Glu Arg Gly Gln Gly Tyr Leu Ala Gly Ser Thr Leu
    210                 215                 220

Ala Gly Trp Ser Ala Tyr Asn Ile Thr Ser Asp Pro Ala Ser Gly Ile
225                 230                 235                 240

Gly Ser Trp Lys Pro Glu Gln Ile Val Gln Tyr Leu Arg Thr Gly Ser
                245                 250                 255

Val Pro Gly Val Gly Gln Ala Ala Gly Pro Met Gly Glu Ala Val Gln
                260                 265                 270

His Ser Phe Ser Arg Met Thr Glu Thr Asp Val Arg Ala Ile Ala Glu
            275                 280                 285

Tyr Leu Arg Thr Val Pro Ala Val Gly Thr Gly Ala Glu Arg Ala Arg
    290                 295                 300

His Asp Trp Gly Lys Pro Ala Thr Asp Val Thr Ala Leu Arg Gly Lys
305                 310                 315                 320

Pro Ile Glu Thr Thr Ile Asp Ala Ala Arg Leu Tyr Leu Gly Asn Cys
                325                 330                 335

Ala Thr Cys His Gln Ala Asp Gly Arg Gly Thr Pro Asp Gly Tyr Tyr
                340                 345                 350

Pro Pro Leu Leu His Asn Ser Thr Val Gly Ala Arg Asp Thr Arg Asn
            355                 360                 365

Leu Val Gln Val Met Leu Asn Gly Ile Glu Arg Lys Ala Gly Asp Arg
    370                 375                 380

His Ile Gly Met Pro Ala Phe Gly Arg Gln Leu Ser Asp Ala Gln Leu
385                 390                 395                 400

Ala Ala Leu Ala Asn Tyr Val Thr Lys Gln Phe Gly Asp Pro Ala Thr
                405                 410                 415

Pro Ala Leu Thr Ala Glu Ala Ile Ala Lys Arg Arg Leu Pro Gln
            420                 425                 430

<210> SEQ ID NO 13
<211> LENGTH: 427
<212> TYPE: PRT
<213> ORGANISM: Ralstonia pickettii

<400> SEQUENCE: 13

Met Lys Ala Ile Ala Ser Phe Ser Leu Leu Leu Ala Gly Pro Leu
1               5                   10                  15

Ala Asn Ala Trp Ala Lys Asp Thr Pro Ala Asp Thr Ala Gln Ile Lys
                20                  25                  30

Arg Gly Glu Tyr Leu Ala Ile Ala Ala Asp Cys Ala Ala Cys His Thr
            35                  40                  45

Ala Pro Gly Gly Lys Pro Phe Ala Gly Gly Leu Pro Met Gln Ile Pro
50                  55                  60

Met Leu Gly Thr Ile Tyr Ser Ser Asn Ile Thr Pro Asp Glu Lys Thr
65                  70                  75                  80

Gly Ile Gly Lys Trp Thr Tyr Glu Glu Phe Glu Arg Ala Val Arg Lys
                85                  90                  95

Gly Val Asp Asp Asp Gly Asn Asn Leu Tyr Pro Ala Met Pro Tyr Pro
                100                 105                 110

Ser Tyr Ala Lys Ile Asn Asp Ala Asp Met Arg Asp Leu Tyr Ala Tyr
            115                 120                 125

Phe Arg Asn Gly Val Thr Ala Val Glu Asn Arg Arg Pro Arg Ser Thr
    130                 135                 140

Ile Arg Trp Pro Leu Asn Met Arg Trp Pro Leu Lys Leu Trp Asn Leu
145                 150                 155                 160
```

Leu Phe Leu Lys Ser Glu Pro Tyr Thr Pro Lys Ser Asp Lys Ser Pro
            165                 170                 175

Thr Trp Asn Arg Gly Ala Tyr Leu Thr Gln Gly Leu Ala His Cys Gly
            180                 185                 190

Thr Cys His Thr Pro Arg Gly Phe Ala Met Gln Glu Lys Ala Leu Asp
            195                 200                 205

Glu Arg Gly Ser Gly Tyr Leu Ala Gly Ser Thr Leu Ser Gly Trp Thr
    210                 215                 220

Ala Phe Asn Ile Thr Ser Asp Pro Thr Ser Gly Ile Gly Ala Trp Lys
225                 230                 235                 240

Pro Glu Gln Leu Val Gln Tyr Leu Arg Thr Gly Ser Val Pro Gly Val
            245                 250                 255

Ala Gln Ala Ala Gly Pro Met Gly Glu Ala Val Gln His Ser Phe Ser
            260                 265                 270

Lys Met Thr Met Gln Asp Val Gln Ala Ile Ala Glu Tyr Leu Arg Thr
            275                 280                 285

Val Pro Ala Val Ser Asn Asn Leu Glu Arg Ala Arg Gln Asp Trp Gly
            290                 295                 300

Lys Pro Ala Thr Asp Val Thr Met Leu Arg Gly Lys Pro Ile Glu Thr
305                 310                 315                 320

Thr Ile Asp Ala Ala Arg Leu Tyr Leu Gly Asn Cys Ala Ser Cys His
            325                 330                 335

Gln Ala Asp Gly Arg Gly Thr Pro Asp Gly Tyr Tyr Pro Pro Leu Leu
            340                 345                 350

His Asn Ser Thr Val Gly Thr Arg Asp Thr Thr Asn Leu Val Gln Val
            355                 360                 365

Ile Leu Phe Gly Ile Glu Arg Lys Ala Gly Asp Lys His Ile Gly Met
            370                 375                 380

Pro Ala Phe Ala Arg Gln Leu Ser Asp Glu Gln Leu Ala Ala Leu Thr
385                 390                 395                 400

Asn Tyr Val Thr Arg Gln Phe Gly Asp Pro Ala Thr Pro Glu Val Thr
            405                 410                 415

Ala Glu Ala Ile Ala Lys Arg Arg Ser Ala Lys
            420                 425

<210> SEQ ID NO 14
<211> LENGTH: 31
<212> TYPE: DNA
<213> ORGANISM: Artificial Sequence
<220> FEATURE:
<223> OTHER INFORMATION: primer

<400> SEQUENCE: 14
acgtagccat ggcacacaac gacaaccact c                           31

<210> SEQ ID NO 15
<211> LENGTH: 27
<212> TYPE: DNA
<213> ORGANISM: Artificial Sequence
<220> FEATURE:
<223> OTHER INFORMATION: primer

<400> SEQUENCE: 15
atcggccgcg cgcgcgaagc ccggcaa                               27

<210> SEQ ID NO 16
<211> LENGTH: 48

```
<212> TYPE: DNA
<213> ORGANISM: Artificial Sequence
<220> FEATURE:
<223> OTHER INFORMATION: primer

<400> SEQUENCE: 16
ttgccgggct tcgcgcgcgc ggccgatctg cgcggtgtcg cgctcgcg              48

<210> SEQ ID NO 17
<211> LENGTH: 48
<212> TYPE: DNA
<213> ORGANISM: Artificial Sequence
<220> FEATURE:
<223> OTHER INFORMATION: primer

<400> SEQUENCE: 17
ttgccgggct tcgcgcgcgc ggccgattat ctcggcaact gcgcgacg              48

<210> SEQ ID NO 18
<211> LENGTH: 42
<212> TYPE: DNA
<213> ORGANISM: Artificial Sequence
<220> FEATURE:
<223> OTHER INFORMATION: primer

<400> SEQUENCE: 18
gtggtgctcg agtgcggccg cgcgcagctt cgcgacgtcc tg                    42

<210> SEQ ID NO 19
<211> LENGTH: 48
<212> TYPE: DNA
<213> ORGANISM: Artificial Sequence
<220> FEATURE:
<223> OTHER INFORMATION: primer

<400> SEQUENCE: 19
gtacgtaagc tttcagtggt ggtggtggtg gtgctcgagt gcggccgc              48
```